US008835352B2

(12) United States Patent
Smyth et al.

(10) Patent No.: US 8,835,352 B2
(45) Date of Patent: Sep. 16, 2014

(54) INDICATOR, APPLICATION THEREOF AND RELATED PRODUCTS

(75) Inventors: Erik Smyth, Dundee (GB); Andrew Mills, Glasgow (GB); David Hazafy, Belfast (GB)

(73) Assignee: Insignia Technologies Limited, Newhouse (GB)

( * ) Notice: Subject to any disclaimer, the term of this patent is extended or adjusted under 35 U.S.C. 154(b) by 49 days.

(21) Appl. No.: 13/379,018

(22) PCT Filed: Jun. 17, 2010

(86) PCT No.: PCT/GB2010/001185
§ 371 (c)(1),
(2), (4) Date: Feb. 17, 2012

(87) PCT Pub. No.: WO2010/146361
PCT Pub. Date: Dec. 23, 2010

(65) Prior Publication Data
US 2012/0142527 A1     Jun. 7, 2012

(30) Foreign Application Priority Data

Jun. 17, 2009   (GB) .................................. 0910464.7

(51) Int. Cl.
*G01N 31/22*     (2006.01)

(52) U.S. Cl.
CPC .................................... *G01N 31/225* (2013.01)
USPC ........ 503/201; 106/31.32; 503/202; 524/577; 525/353

(58) Field of Classification Search
CPC .................................... G01N 31/225
USPC ................ 503/200–226; 106/31.32; 524/577; 525/353

See application file for complete search history.

(56) References Cited

U.S. PATENT DOCUMENTS

| 3,533,750 A | 10/1970 | Belisle |
| 2008/0286154 A1 | 11/2008 | Kane |

FOREIGN PATENT DOCUMENTS

| EP | 0611966 A1 | 8/1994 |
| EP | 1598667 A1 | 11/2005 |
| GB | 2452977 A | 3/2009 |
| WO | 03021252 A1 | 3/2003 |

OTHER PUBLICATIONS

Written Opinion and International Search Report from related PCT Application No. PCT/GB2010/001185.

*Primary Examiner* — Bruce H Hess
(74) *Attorney, Agent, or Firm* — Benesch, Friedlander, Coplan & Arnoff, LLP; Thomas Y. Kendrick; Benjamen E. Kern

(57) ABSTRACT

There is disclosed an indicator composition, the application thereof to substrates, and related products. The indicator composition comprises an organic solvent soluble polymer and a redox sensitive material which displays different visible properties in the oxidized and reduced forms. The organic solvent soluble polymer can be at least partially sulfonated polystyrene. The indicator composition can be dissolved in organic solvents such as acetone, ethanol and ethyl acetate to form inks which can be used in a variety of printing processes. The indicator composition can be used to detect oxidizing agents, oxygen, water, reducing agents, UV light, temperature and the passage of time.

25 Claims, No Drawings

INDICATOR, APPLICATION THEREOF AND RELATED PRODUCTS

CROSS-REFERENCE TO RELATED APPLICATIONS

This application is a National stage entry under 35 U.S.C. §371 of PCT Patent Application No. PCT/GB2010/001185, filed Jun. 17, 2010, which claims priority to United Kingdom Patent Application No. GB 0910464.7, filed on Jun. 17, 2009, each of which is hereby incorporated by reference.

FIELD OF INVENTION

The present invention relates to an indicator, a method for applying an indicator to a printing substrate, and products derived therefrom. In particular, the present invention relates to a UV activated oxygen and/or water sensitive ink, and to a method for applying the ink to a blank for a package, or to a printing substrate for forming a blank for a package. The products derived therefrom include, for example: a printing substrate, a blank, and a package to which the ink has been applied. Further products may include, for example, a time-temperature history indicator. The indicator composition can be used to detect oxidising agents, oxygen, water, reducing agents, UV light, temperature and the passage of time.

Perishable goods, and in particular drinks and foodstuffs, are often provided in some form of air-tight packaging. This packing can be applied in a modified atmosphere (known as modified atmosphere packaging (MAP)), which limits the presence of oxygen. Alternatively, perishable goods may be packaged in normal atmospheric conditions.

Items that are packaged in air-tight packaging include: food, beverages, works of art, pharmaceuticals, medical diagnostic kits and sterilised packages. As mentioned, it is particularly desirable in the food industry to package goods such that their exposure to oxygen after packaging is minimised. This can be used to effectively extend the shelf life of many perishable items.

BACKGROUND ART

It is useful to be able to determine the length of time for which a package containing perishable goods has been opened. To this end, many different sensors for detecting oxidising agents, and in particular for detecting oxygen, have been produced. Several of these sensors have been adapted for attachment to packages containing perishable goods. For example, GB 2419868, FR 2836677, WO 2006/077413, GB2344101 and US 2006/0110835 disclose the use of oxygen sensitive dyes that are covered by a seal, the seal being broken by the opening of a package, and the dye changing colour over a set period of time to indicate the duration for which the package has been opened.

WO 03/021252 (incorporated herein by reference) discloses a sensor for oxidising agents which is activated using UV light. This patent application discusses the use of a particular chemical composition which can be in the form of an ink, and which may be printed onto a variety of supports. However, the indicator disclosed is necessarily sensitive to oxygen. It is not apparent from reading the application how such an indicator may be effectively integrated with, or printed onto, packaging in the reduced form. In addition, it is unclear as to how such an indicator may be applied in the reduced form in atmospheric conditions.

The composition described in WO 03/021252 comprises at least one redox-sensitive material, at least one semiconductor material and at least one electron donor. The intimate contact of the various components of the indicator allows the redox sensitive material to undergo a redox reaction wherein there is a transfer of electrons from the photogenerated reduced form of the semiconductor material to the redox sensitive material.

The redox-sensitive material can be a dye such as a thiazine dyestuff, an oxazine dyestuff, an azine dyestuff, a triphenylmethane dyestuff, an indophenol dyestuff, an indigo dyestuff, viologen and/or mixtures thereof.

The semiconductor material has the ability to form an excited electronic state that is sufficiently oxidising to oxidize the sacrificial electron donor and has a reduced form that is able to reduce the redox sensitive material.

The semiconductor material may be an oxide of titanium (such as titanium (IV) oxide; $TiO_2$, and strontium titanate; $SrTiO_3$), tin (such as tin (IV) oxide; $SnO_2$), tungsten (such as tungsten (VI) oxide; $WO_3$) and zinc (such as zinc (II) oxide; ZnO) and mixtures thereof.

The electron donor has the ability to donate electrons, preferably irreversibly. Typically, the electron donor is a mild reducing agent. The electron donor may, for example, be an amine (e.g. NaEDTA and TEOA), reducing saccharide (such as glucose and fructose), readily oxidisable polymer (such as polyvinyl alcohol), and other general anti-oxidant (such as ascorbic and citric acid) or easily oxidizable material (such as glycerin) and/or mixtures thereof.

The indicator may further comprise a binder which binds all the components together. The binder may be a polymeric material such as gelatin, hydroxyethyl cellulose (HEC), polyvinyl alcohol (PVA), ethyl cellulose (EC), cellulose acetate (CEA), polypyrolidone (PVP), polyethylene oxide, and polymethylmethacrylate (PMMA).

Many modern day printing processes, and many types of modern packaging, require the use of organic solvent based inks. Whilst it is stated in WO 03/021252 that the indicator compositions can be combined with an organic solvent to provide an ink or printable solution, the inventors have found that the redox active species tends to leach out of such solutions. For example, the polymers described as binders are generally water soluble (such as polyvinyl alcohol), as are the redox active species (such as methylene blue). When these compositions are added to organic solvents the dye (redox active species) and the polymer do not dissolve well. Furthermore, on exposure of the indicator compositions described in WO 03/021252 to water or moisture (as is normally present to at least some degree in organic solvents and in the atmosphere), the dye in particular tends to leach out of solution. As the dye leaches out of solution the ink degrades and becomes much less effective (less coloured) and more difficult to bleach. Furthermore, the lifetime of the ink becomes more difficult to predict, limiting the use of the ink in, for example, time temperature indicators. Therefore, the indicator compositions described in WO 03/021252 tend to break down on addition to an organic solvent, and on contact with water. Such compositions are therefore inherently unstable.

Generally a composition comprising the indicator compositions of WO 03/021252 will be unstable upon addition to, for example, food packaging. Typically, such a composition will break down upon addition to food packaging as the dye contained therein, upon contact with water contained in the food packaging or the atmosphere, will tend to leach out of the composition. Furthermore, the redox active species can leach out of solution following storage under ambient conditions, meaning that a solution of the composition is not suitable for use in printing.

The inks and indicator compositions described in WO 03/021252 are therefore not suitable for use in many modern day printing processes, which require the use of organic solvent based inks, or in the application to many types of modern packaging, which require that the compositions are stable (i.e., resistant to leaching) on exposure to water. Moreover, it is not apparent how a charged, water soluble, redox active species (such as methylene blue) may be incorporated with a high degree of permanence into an organic solvent soluble indicator composition suitable for use in many modern day printing processes.

Furthermore, it can be impractical to activate indicator compositions (incorporated into inks) after they have been printed and sealed on a substrate, such as packaging. For example, it can be difficult to expose the printed indicator composition to the correct amount of UV light in a controlled fashion, particularly as most printing processes do not have the time window to allow such exposure. Also, exposing the indicator composition to UV light after printing and sealing requires additional specialised equipment to be used in the printing process, and makes the process more complicated and time-consuming. Known UV activatable inks are unsuitable for activation before printing as they will change colour (i.e., oxidise) before or during the printing process.

Therefore, it is an object of the present invention to obviate or mitigate at least some of the disadvantages of the prior art.

A further object of the invention is to provide a method for applying an oxygen sensitive ink to a printing substrate.

A still further object of the invention is to provide an indicator ink that can be used in modern day printing processes.

DISCLOSURE OF INVENTION

According to a first aspect of the present invention there is provided an indicator for detecting at least one of an oxidising agent and water, the indicator comprising an organic solvent soluble polymer and a redox sensitive material which displays different visible properties in the oxidised and reduced forms, wherein the redox sensitive material in the oxidised form is bound to the organic solvent soluble polymer by ionic bonding.

The indicator is in the form of a composition. The indicator, or indicator composition, may be UV light activatable.

The indicator of the present invention contains an ion-paired dye (the oxidised, positively charged dye can ion pair with the negatively charged polymer). Surprisingly, the inventors have found that this ion-paired dye bleaches (or reduces) more completely and more quickly than the same dye which is not ion paired. This allows the indicator composition of the present invention to be activated more quickly and more completely than known indicators incorporating redox dyes.

The indicator of the present invention also allows a large amount of dye to be incorporated, yet shows significant resistance to leaching, even in the presence of water. Furthermore, the indicator is soluble in, and compatible with, organic solvents such as acetone and ethyl acetate. This makes the ink, from which the indicator is derived, more stable when stored for relatively long periods of time, and more suitable for use with modern day printing processes.

Furthermore, once reduced, the indicator composition of the present invention takes typically hours or days (depending on the ambient conditions, especially temperature) to oxidise back to its original colour. Furthermore, the rate of oxidation of the composition of the present invention is highly predictable and controllable. These aspects mean that the indicator composition is particularly useful in indicating the freshness of foodstuffs and the like.

Also, the inventors have found that when the ink of the present invention is applied to packaging as an indicator composition, the composition shows very low levels of migration through the substrate to which it is applied. This is advantageous for the packaging industry, and particularly the food packaging industry, as the composition has less tendency to migrate through packaging, and therefore is less likely to contaminate the food or drink contained therein.

In addition, the inventors have found that the ink of the present invention is sufficiently stable and long lasting in the reduced form, that it can be reduced before being used in the printing process, obviating the need to integrate a reduction step into the printing process.

Water may be in the form of moisture in the atmosphere, typically having a Relative Humidity $\geq 10\%$ at $20°$ C.

The organic solvent soluble polymer may comprise a hydrophobic backbone and a plurality of electronically charged sidechains. The organic solvent soluble polymer may be at least partially-sulfonated polystyrene.

The at least partially-sulfonated polystyrene may be from about 10% to about 30% sulfonated. Typically, the at least partially-sulfonated polystyrene has the formula ([sulfonated polystyrene unit]$_{0.1\ to\ 0.3x}$[polystyrene unit]$_{1-x}$)$_n$.

The redox sensitive material can be selected from one or more of the group consisting of: a thiazine dyestuff, an oxazine dyestuff, an azine dyestuff, a triphenylmethane dyestuff, an indophenol dyestuff, an indigo dyestuff and viologen. Typically, the redox sensitive material is methylene blue.

According to one aspect of the present invention, the indicator is suitable for detecting an oxidising agent and comprises about 50% by weight to about 57% by weight organic solvent soluble polymer and from about 0.35% by weight to about 3.4% by weight redox sensitive material. The % by weight figures are in the absence of solvent. Typically the indicator comprises an at least partially-sulfonated polystyrene having the formula ([sulfonated polystyrene unit]$_{0.1\ to\ 0.3x}$[polystyrene unit]$_{1-x}$)$_n$.

Advantageously the indicator comprises methylene blue.

According to one aspect of the present invention, the indicator is suitable for detecting water and comprises about 50% by weight to about 57% by weight organic solvent soluble polymer and from about 0.35% by weight to about 3.4% by weight redox sensitive material. The % by weight figures are in the absence of solvent. Typically the indicator comprises an at least partially-sulfonated polystyrene having the formula ([sulfonated polystyrene unit]$_{0.1\ to\ 0.3x}$[polystyrene unit]$_{1-x}$)$_n$.

Advantageously the indicator comprises methylene blue.

The indicator may be supported on an inert material such as glass, paper, fabric, ceramic or metal.

Optionally, the inert material comprises a coating configured to seal at least a portion of the inert material having the indicator applied thereto.

Optionally the coating provides a seal having a very low oxidising agent permeability thereby preventing oxidation of the indicator.

According to one embodiment, the coating provides a semi-permeable seal configured to allow controlled flow of oxidising agent to the indicator.

The seal may be selected from one or more of the group consisting of: PET, EVOH, PVDC, PVA or regenerated cellulose.

Optionally the seal is configured to be selectively removable.

The oxidising agent may be oxygen.

Optionally the indicator is in the form of an ink. Typically, the indicator is dissolved in an organic solvent to form an ink. The ink may be applied to a printing substrate in the form of a LOGO or text.

When the indicator is in the form of an ink, it may comprise the following components in the following amounts: 6 to 13% by weight organic solvent soluble polymer; 0.1 to 1.2% by weight redox sensitive material; 4.8 to 9.5% by weight electron donor; 2.0 to 3.8% by weight semiconductor material; 60 to 76% by weight organic solvent; and 0 to 25% by weight aqueous solvent (such as water).

It will be understood that the amounts of each component can be varied within the ranges given depending on the type of ink desired and the type of solvent being used. For example, larger quantities of redox sensitive indicator and optionally water can be incorporated with ethanol based inks. The organic solvent soluble polymer, redox sensitive material, electron donor, semiconductor material, organic solvent and aqueous solvent (for example water) can be selected from those described herein.

Generally the indicator is ≥17 weight percent (wt %) soluble in an organic solvent such as acetone, ethanol or ethyl acetate. Typically the ink of the present invention is stable upon storage. Generally the ink is stable upon storage for at least six months under dark, but otherwise ambient, conditions. Suitably at least 99% of the redox sensitive material remains in solution following such storage, more suitably substantially all of the redox sensitive material remains in solution.

The indicator may further comprise an electron donor. The electron donor may be a mild reducing agent, such as an amine, a reducing saccharide, a readily oxidisable polymer, or other general anti-oxidants.

In particular, the electron donor may be selected from one or more of the group consisting of: NaEDTA, TEOA, glucose, fructose, a polyol, in particular glycerol, trihydroxyhexane, ascorbic acid or citric acid.

Typically the indicator comprises about 28% by weight to about 35% by weight electron donor (in the absence of solvent).

The indicator may further comprise at least one semiconductor material specifically sensitive to light having a wavelength of about 200-400 nm, and wherein upon irradiation of said semiconductor material by light having a wavelength of about 200-400 nm an electron is donated by the electron donor to the semiconductor material which in turn provides an electron to the redox sensitive material causing the redox sensitive material to become reduced.

Typically the indicator comprises about 11% by weight to about 14% by weight semiconductor material (in the absence of solvent).

The semiconductor material may be an oxide of: titanium, tin, tungsten, zirconium, and zinc and mixtures thereof.

In particular the semiconductor material may be selected from one or more of the group consisting of: titanium (IV) oxide ($TiO_2$), strontium titanate ($SrTiO_3$), tin (IV) oxide ($SnO_2$), tungsten (IV) oxide ($WO_3$), zirconium (IV) oxide ($ZrO_2$), and zinc (II) oxide (ZnO) and mixtures thereof.

Preferred semiconductors are ones that are not very sensitive to UVA light, but that are sensitive to UVB light, since UVA light is present at reasonably high levels in sunlight and, sometimes, in ambient food cabinet light. This means a large bandgap semiconductor is preferred such as, for example, nanorutile titania or tin oxide.

The indicator described herein can be applied to printing substrates (such as paper and card) used in the manufacture of blanks and packages.

Optionally the printing substrate is configured to prepare a blank for use in the manufacture of a package.

According to a further aspect of the invention there is provided a method of detecting exposure to at least one of an oxidising agent and water, comprising the steps of:
a) providing an indicator as described herein, said indicator comprising an organic solvent soluble polymer and a redox sensitive material;
b) activating the indicator by reducing the redox sensitive material so as to convert the redox sensitive material into its reduced form; and
c) subsequently detecting a visible change in the indicator, whereby exposure to an oxidising agent or water is revealed.

The reduction can be carried out by irradiating with light of about 200 to about 400 nm.

Water can be in the form of moisture, water vapour, or relative humidity, the relative humidity typically being 10%.

Optionally the method comprises the further step of removing a seal from the indicator to expose the indicator to at least one of an oxidising agent and water.

Typically, the indicator is exposed to both an oxidising agent and water.

According to a further aspect of the present invention there is provided an indicator for detecting when an object has been subject to an increase in temperature for a set period of time comprising the indicator as described herein.

According to a further aspect of the present invention there is provided a method of detecting when an object has been subject to an increase in temperature for a set period of time comprising the steps of:
a) providing to the object the indicator as described herein;
b) activating the indicator by reducing the redox sensitive material so as to convert the redox sensitive material into its reduced form; and
c) subsequently detecting a visible change in the indicator, whereby exposure to an increase in temperature is revealed.

The reduction can be carried out by irradiating with light of about 200 to about 400 nm.

When the indicator is frozen (i.e., subject to temperature <−20° C.), it loses its ability to respond to oxidising agents, but the sensitivity to oxidising agents is restored on exposing the indicator to warmer temperatures. This enables the indicator to be used in time-temperature indicators.

Time-temperature indicators operate by showing (once activated) no optical effect over a desired period at, or below, a desired temperature (say 4° C. for an indicator for a refrigerated item, and −20° C. for an indicator for a frozen item). However, time-temperature indicators do show an optical effect over the same desired period if the temperature of the indicator (and the item to which it is applied) exceeds a predetermined minimum temperature. Thus, time-temperature indicators can be used to show an item has been exposed to a temperature above the recommended minimum temperature for storage. For example, a time-temperature indicator can show that an item has been defrosted and re-frozen.

The method may comprise the indicator as described herein.

Alternatively, the method may comprise an indicator as described in WO 03/021252. Such an indicator comprises redox sensitive material which displays different visible properties in the oxidised and reduced forms; an electron donor; and a semiconductor material specifically sensitive to light of about 200-400 nm, and wherein upon irradiation of said semi-conductor material by light of about 200-400 nm an electron is donated by the electron donor to the semiconductor material which in turn provides an electron to the redox sensitive material causing the redox sensitive material to become reduced.

In a further aspect of the invention there is provided an indicator for detecting exposure to light of about 200 to 400 nm comprising an indicator as described herein.

According to a further aspect of the present invention there is provided a method of detecting exposure to UV light comprising the steps of:
a) providing an indicator as described herein;
b) activating the indicator by exposure to an oxidising agent and water to convert the redox material into its oxidised form; and
c) subsequently detecting a visible change in the indicator, whereby exposure to light of about 200 to 400 nm is revealed.

According to a further aspect of the invention there is provided a method of detecting exposure to water comprising the steps of:
a) providing an indicator comprising:
   a redox sensitive material which displays different visible properties in the oxidised and reduced forms;
   an electron donor; and
   a semiconductor material specifically sensitive to light of about 200 to 400 nm;
b) activating the indicator by irradiating with light of about 200 to 400 nm so as to convert the redox material into its reduced form; and
c) subsequently detecting a visible change in the indicator, whereby exposure to water is revealed.

The method may comprise the indicator as described herein.

Under very dry conditions (typically <10% relative humidity at 20° C.), the indicator ceases to respond to oxidising agents, but the sensitivity to oxidising agents is restored on exposure to air with a relative humidity ≥10%. The indicator can be reduced, or activated/bleached, at very low humidity (<10% relative humidity) using UV light. However, under these low humidity conditions (such as found in dry foods, or in vacuum packed foods) the indicator will not effect a visible change in the presence of an oxidising agent, such as oxygen. Thus water, usually as a vapour, can be used to trigger the indicator. For example, a colourless (i.e., activated) film in air, at a relative humidity <10% at 20° C. will change colour (i.e., oxidise) on exposure to ambient air with a relative humidity ≥10%.

A method of applying an oxidising agent and/or water indicator to a printing substrate, the method comprising the steps of:
a) activating the indicator as described herein by reducing the redox sensitive material so as to convert the redox sensitive material into its reduced form;
b) providing a printing substrate to a printing assembly;
c) applying to the printing substrate the activated indicator; and
d) providing a coating configured to seal at least a portion of the printing substrate having the activated indicator applied thereto.

The coating of step d) can be a layer of the printing substrate placed on top of the activated indicator. For example, after the activated indicator is applied, the printing substrate can be configured into a roll or reel, with each layer of the roll or reel acting as a coating or barrier for the activated indicator with which it is in contact.

This method enables the stable compositions of the present invention to be activated before printing. Due to their stable nature, the compositions of the present invention can be used in the reduced state, and in a normal atmosphere printing process, without appreciably oxidising. Therefore, there is no requirement to apply UV light to printed packages, as the ink contained therein is already activated. This removes the need for additional specialist equipment during printing, and obviates the problem of fitting an activation step into the printing process.

According to further aspect of the present invention there is provided a method of applying an oxidising agent and/or water indicator to a printing substrate, the method comprising the steps of:
a) providing a printing substrate to a printing assembly;
b) applying to the printing substrate the indicator as described herein;
c) providing a coating configured to seal at least a portion of the printing substrate having the indicator applied thereto; and
d) activating the indicator by reducing the redox sensitive material so as to convert the redox sensitive material into its reduced form.

The reduction can be carried out by exposing the indicator to light having a wavelength of about 200-400 nm.

The printing methods may be carried out in the presence of oxygen, and in particular may be carried out in atmospheric conditions. This is in contrast to known methods of applying indicators for detecting oxidising agents.

Such known methods must generally be carried out in an atmosphere having a reduced oxygen content. This increases the cost and inconvenience of such known methods. Furthermore, if the amount of oxygen present in the atmosphere is not sufficiently low, the reliability of the indicator may be adversely affected. Therefore, the method disclosed herein is more cost effective than known methods. Also, the printing methods enable activation of the indicator at any time as chosen by the manufacturer. For example, the activation may take place some time after the printing process, and printed packages can be stored and transported in normal atmospheric conditions. Alternatively, using the first printing method, the indicator can be activated before printing commences.

The redox sensitive material can be selected from one or more of the group consisting of: a thiazine dyestuff, an oxazine dyestuff, an azine dyestuff, a triphenylmethane dyestuff, an indophenol dyestuff, an indigo dyestuff and viologen. Typically, the redox sensitive material is methylene blue.

Preferably the coating provides a seal having a very low oxidising agent permeability thereby preventing oxidation of the indicator.

According to one embodiment, the coating provides a semi-permeable seal configured to allow controlled flow of oxidising agent to the indicator.

The seal or seals act as a barrier and may be part of a barrier layer.

The seal may be selected from one or more of the group consisting of: PET, EVOH, PVDC, PVA or regenerated cellulose.

Preferably the seal is configured to be selectively removable.

The oxidising agent may be oxygen. Preferably the indicator is in the form of an ink.

Optionally the indicator or ink is applied to the printing substrate in the form of a LOGO or text.

The indicator may further comprise an electron donor. The electron donor may be a mild reducing agent, such as an amine, a reducing saccharide, a readily oxidisable polymer, or other general anti-oxidants.

In particular, the electron donor may be selected from one or more of the group consisting of: NaEDTA, TEOA, glucose, fructose, a polyol, such as glycerol, ascorbic acid, trihydroxyhexane or citric acid.

The indicator may further comprise at least one semiconductor material specifically sensitive to light having a wavelength of about 200-400 nm, and wherein upon irradiation of said semiconductor material by light having a wavelength of about 200-400 nm an electron is donated by the electron donor to the semiconductor material which in turn provides an electron to the redox sensitive material causing the redox sensitive material to become reduced.

The semiconductor material may be an oxide of: titanium, tin, tungsten, zirconium, and zinc and mixtures thereof.

In particular the semiconductor material may be selected from one or more of the group consisting of: titanium (IV) oxide ($TiO_2$), strontium titanate ($SrTiO_3$), tin (IV) oxide ($SnO_2$), tungsten (IV) oxide ($WO_3$), zirconium (IV) oxide ($ZrO_2$), and zinc (II) oxide (ZnO) and mixtures thereof.

In one embodiment, a printing substrate is prepared wherein a portion of the seal covering the indicator is detachable from the printing substrate by a user. For example, when the printing substrate is configured as a fruit drink package, the portion of the seal is attached to the lid of the package, and is automatically removed from the package when the package is opened by a user. Therefore, the seal is configured to be selectively removable.

The method of the present invention enables application of an oxygen sensitive indicator in the oxidised form, and potentially in the presence of oxygen. Once applied to a printing substrate, the indicator is sealed using a material that inhibits oxygen, or oxidising agents, from reacting with the indicator. After sealing, the indicator is exposed to UV light which converts the indicator to the reduced form. The indicator remains sealed from the atmosphere until such time that the package is opened, at which point the seal is broken or removed thus exposing the indicator to the atmosphere. Once exposed to the atmosphere, the indicator will change colour at a particular rate dependent on the particular composition of the indicator, and optionally the temperature.

This same method can be used to apply a water sensitive indicator, a time temperature indicator or a security indicator.

Alternatively, the seal may be semi-permeable, and may be configured to allow ingress of an oxidising agent at a predetermined rate, without the requirement of removing or breaking the seal.

In one embodiment, the present invention enables the application of an oxygen sensitive ink to a printing substrate using commonplace printing techniques. There is no requirement for the atmosphere to be modified, as is the case with modified atmosphere packaging. However, it will be appreciated that the technique could also be used in a modified atmosphere packaging process.

The printing methods described herein are used in the manufacture of printing substrates (such as paper and card), blanks and packages.

Optionally the printing substrate is configured to prepare a blank for use in the manufacture of a package.

According to a further aspect of the present invention there is provided a printing substrate obtainable according to the printing methods as described herein.

According to a further aspect of the present invention there is provided a method for manufacturing a blank for a package comprising an indicator as described herein, the method comprising the steps of:
a) providing a printing substrate comprising a blank to a printing assembly;
b) applying to the blank the indicator as described herein;
c) providing a coating configured to seal at least a portion of the blank having the indicator applied thereto; and
d) activating the indicator by reducing the redox sensitive material so as to convert the redox sensitive material into its reduced form.

The reduction can be carried out by exposing the indicator to light having a wavelength of about 200-400 nm.

According to a further aspect of the present invention there is provided a blank obtainable according to the method as described herein.

According to a still further aspect of the present invention there is provided a method for manufacturing a package comprising a UV activatable oxidising agent and/or water indicator, the method comprising the steps of:
a) providing a printing substrate comprising a blank to a printing assembly;
b) applying to the blank a UV activatable oxidising agent and/or water indicator as described herein;
c) providing a coating configured to seal at least a portion of the blank having the indicator applied thereto;
d) activating the indicator by reducing the redox sensitive material so as to convert the redox sensitive material into its reduced form; and
e) arranging the blank to form a package.

The reduction can be carried out by exposing the indicator to light having a wavelength of about 200-400 nm.

According to a further aspect of the present invention there is provided a package obtainable according to the method as described herein.

The present invention will now be described by way of example only.

MODES FOR CARRYING OUT THE INVENTION

Most colourimetric oxygen indicators rely on a reaction between a redox-sensitive indicator dye, such as methylene blue, and a strong reducing agent, such as glucose in a strongly alkaline (pH>12) environment. This reaction leads to the reduction of the redox-sensitive dye and concomitant colour change. The redox dye is readily reoxidised back to its original colour upon exposure to oxygen. Known indictors comprising a redox-sensitive dye, a sacrificial electron donor and a semiconductor photoactive material have been described for the detection of oxygen in WO 03/021252. However, such dyes are not usable in most organic solvents, as the redox-sensitive dye used tends to leach out of solution.

Although the following discussion is limited to that of oxygen it should be realised that the discussion is applicable to any other type of oxidising agents.

The novel oxygen indicator described utilises at least one redox-sensitive dye (eg. a thiazine dyestuff, oxazine dyestuff, azine dyestuff, triphenylmethane dyestuff, indophenol dyestuff, indigo dyestuff, viologen or a mixture thereof). The redox-sensitive dye is chosen so that, at the levels employed in the oxygen indicator, it has little or no absorbance in the near UV, i.e. 300-400 nm. The redox-sensitive dyestuff is also chosen so that its reduced form has a different colour, and/or fluorescence, to its oxidised form and is oxidised to the latter by oxygen.

The oxygen indicator utilises a sacrificial electron donor (SED), which is a mild reducing agent, such as a polyol, in particular glycol, or triethanolamine (TEOA), or the disodium salt of ethylenediamine tetraacetic acid (NaEDTA). The mild reducing agent is selected on the basis that, at the levels employed in the oxygen indicator, it: (a) does not reduce the redox-sensitive dye at a significant rate under either aerobic or anaerobic conditions and (b) does not reductively quench the electronically excited state of the redox-sensitive dye under either aerobic or anaerobic conditions. These conditions being satisfied, the combination of redox-sensitive dye and mild reducing agent is stable and long-lived under ambient atmospheric and typical room-light conditions. Note that no strong alkaline material is present in the oxygen indicator since the latter turns many mild reducing agents, such as reducing sugars, TEOA and NaEDTA into strong reducing agents, and conditions (a) and (b) would no longer be satisfied.

A near UV-absorbing semiconductor photoactive material (SC) is also present in the oxygen indicator. The role of the semiconductor is to initiate the process of indicator activation by absorbing some of the burst of near UV light that the indicator is exposed to. Absorption of a photon of near UV light by the semiconductor material in particle, film (micro or nanocrystalline) or single crystal form leads to the creation of a photogenerated electron-hole pair.

The semiconductor material is selected so that the photogenerated electron is sufficiently reducing in power that it can reduce the redox-sensitive dye present and the hole is sufficiently oxidising that it can oxidise the mild reducing agent present. The net effect upon UV activation of the combination of semiconductor material/redox-sensitive dye/sacrificial electron donor that goes to make the oxygen indicator is that the dye is converted to its differently coloured, or fluorescent, reduced, oxygen-sensitive, form. For example, methylene blue (which is blue) is reduced to leuco-methylene blue (which is colourless) and the sacrificial electron donor, or mild reducing agent, is oxidised, i.e. SED to SEDox; both latter species are usually colourless.

The overall scheme can be represented by the following series of reaction equations:
Light Activation Step (Under Anaerobic Conditions)

$$SC + h\nu \rightarrow SC(e^-;h^+)$$

Where hv represents the energy of an absorbed photon; the latter will have an energy greater than or equal to the bandgap energy of the semiconductor (SC), i.e. an ultra-bandgap photon. For the present invention the most favoured semiconductors will have large bandgaps (3-4 eV) and so will require excitation by near UV light. SC ($e^-$; $h^+$) represents an electronically excited form of the semiconductor, SC, and will have a photogenerated electron, SC ($e^-$), and a photogenerated hole, SC ($h^+$) available for reaction.
Scavenging of the Photogenerated Electron $$SC(e^-;h^+) + Ox \rightarrow Red + SC(h^+)$$

Where Ox is the aerobically (and anaerobically) stable, coloured form of the redox sensitive dye and Red is the reduced form of Ox which not only is markedly different in colour, and/or fluorescence, to Ox but also reacts readily with oxygen and, consequently, is only stable under anaerobic conditions.
Scavenging of the Photogenerated Hole $$SC(h^+) + SED \rightarrow SC + SED^+$$

The mild reducing agent, SED, is chosen so that it does not react directly with Ox, as is the case for most other colourimetric oxygen indicators, and so that it preferably reacts irreversibly with the photogenerated hole.
Oxygen Indicating Step $$Red + O_2 \rightarrow Ox + H_2O$$

The reduced form of the redox sensitive dye is stable under anaerobic conditions. However, upon exposure to oxygen the reaction noted above takes place and the original colour (i.e. that seen before light activation) and/or fluorescence of the indicator returns, thus indicating the presence of oxygen.

In one embodiment of the present invention the indicator also comprises an organic solvent soluble polymer which can bind the redox-sensitive material by ionic bonding, at least when the redox-sensitive material is in the oxidised form. The polymer can have a hydrophobic backbone and electronically charged sidechains. For example, the polymer can be partially-sulfonated polystyrene or another suitable polymer that has at least some electronically charged, or sufficiently polar, sidegroups that have sufficient affinity for the redox dye to mitigate leaching of the dye under storage or on exposure to organic solvents or water, to produce an ink that is useable in the printing process.

The oxygen indicator can be re-used simply by reactivating with ultra-bandgap light, the preferred wavelength range of which falls in the near UV. Note that the oxygen indicator is not selective towards oxygen, but will also respond to most strong oxidising agents if they are present, such as chlorine, nitrogen dioxide and ozone.

This lack of selectivity towards oxygen is also a feature of almost all other oxygen indicators. Fortunately, in most packages (especially food) and the ambient environment, there are no, or very little, oxidising agents other than oxygen. The sensitivity of the oxygen indicator towards oxidising gases other than oxygen may be exploited to create indicators for these other gases.

The oxygen sensing action of the oxygen indicator is irreversible in that it only works after it has been activated by exposure to near UV light. Once oxidised, it cannot be reactivated unless it is deliberately exposed again to near UV light.

Typical ambient room light does not possess sufficient UV light to drive this light activation process at a significant rate. Although prolonged exposure to sunlight can drive the light activation step forward, most packaged goods, including food, also suffer unwanted deleterious effects if exposed to bright sunlight. As a consequence, under the typical lighting conditions employed in handling most packaged goods, the oxygen indicator will not be activated.

The dyestuff brings about the colour change exhibited. The dyestuffs that can be used include: thiazine dyestuffs (such as: methylene blue, thionin and toluidine blue), oxazine dyestuffs (such as: resazurin, safranine O, and celestine blue), azine dyestuffs, (such as: and cresyl violet acetate and azure A), indophenol dyestuffs (such as dichloroindophenol), indigo dyestuffs (such as; indigo and indigo carmine), viologens (such as heptyl and benzyl viologen) and mixtures thereof.

The organic solvent soluble polymer binds with the dyestuff to ensure that the dyestuff remains soluble in organic solvent. Organic solvent soluble polymers that can be used include partially-sulfonated polystyrene or another suitable hydrophobic, anionic, organic solvent soluble polymer.

The semiconductor material drives the reduction of the redox-sensitive dye by the sacrificial electron donor, upon absorption of some of the near UV light used to activate, i.e. make sensitive towards oxygen, the oxygen indicator. The semiconductor material may be used in various forms, including: as micro and nanocrystalline powder particles dispersed in a polymer encapsulating material or pressed in the form of a tablet or pellet, or as a micro or nanocrystalline film. The semiconductor material is usually biologically and chemically inactive, unless irradiated with light of energy greater than or equal to its bandgap. Ideally, the bandgap of the semiconductor should fall in the near UV region, i.e. 3.1 to 4.1 eV (400 to 300 nm). Typically the semiconductor should be selected from a group that includes the oxides of titanium (such as titanium (IV) oxide; $TiO_2$, and strontium titanate; $SrTiO_3$), tin (such as tin (IV) oxide; $SnO_2$), tungsten (such as tungsten (VI) oxide; $WO_3$) and zinc (such as zinc (II) oxide; ZnO) and mixtures thereof. The sacrificial electron acceptor is any species that reacts readily with the photogenerated hole on the semiconductor but does not react directly or significantly with either the redox-sensitive dye (under aerobic or anaerobic conditions) or with oxygen (under aerobic conditions).

Examples of such a sacrificial electron donor can be found amongst the following categories: amines (such as NaEDTA and TEOA), reducing saccharides (such as glucose and fructose), readily oxidisable polymers, and other general anti-oxidants (such as ascorbic and citric acid), polyols (such as glycerol), trihydroxyhexane and mixtures thereof. Although some of the above are sometimes cited as examples of strong reducing agents (such as glucose and TEOA), this is only the case if a strong alkali is also present. In the present invention no strong alkali is used and all sacrificial electron donors cited above are as a consequence only mildly reducing.

When combined with a suitable solvent, the initial form of the oxygen indicator is as an ink or castable solution that can be printed or cast on a wide variety of supports. Examples of typical solvents that can be used include: ketones (such as acetone), alkylhalides (such as chloromethane), esters (such as ethyl acetate) and aromatics (such as toluene).

GENERAL EXAMPLE

A solvent based ink, according to one embodiment of the present invention, and comprising sulfonated-polystyrene (a polymer binder), glycerol (a sacrificial electron donor), nanorutile titanium dioxide (a photocatalyst) and methylene blue (a dye) was prepared as described below.

Preparation of Sulfonated Polystyrene

The sulfonated polystyrene (SPS) used was prepared in-house by the direct sulfonation of polystyrene as described in previous literature (C. R. Martins et al, Journal of the Brazilian Chemical Society, 14 (2003) No. 5; Makowski et al, U.S. Pat. No. 3,870,841 (1975); R. A. Weiss et al, Journal of Polymer Science Polymer Chemistry Edition, 23 (1985) pp 525-533).

Initially, 52 g of polystyrene (average molecular weight 250,000, supplied by Acros Organics) was placed in a 3-necked, round-bottomed flask and to it was added 245 mL of dichloromethane (DCM). The solution was stirred vigorously on a magnetic stirrer to promote dissolution of the polymer, typically requiring 1 to 2 hours for complete dissolution.

Whilst the polystyrene was dissolving, acetyl sulphate (which acts as the sulfonating agent) was prepared. 49 mL of DCM was placed in a conical flask sealed with a rubber septum stopper, and to it was carefully added 9.5 mL of acetic anhydride via a syringe. The resulting solution was immediately placed under an argon atmosphere and cooled using an ice bath. Once sufficiently cool, and once the polystyrene had dissolved in the DCM, 3.5 mL of 95% sulphuric acid was added dropwise to the DCM/acetic anhydride mixture, thus converting the acetic anhydride to acetyl sulphate. Once all of the sulphuric acid had been added, the acetyl sulphate was removed from the argon atmosphere. 35 mL of acetyl sulphate was then extracted and subsequently added to the stirred polystyrene solution.

After addition of the acetyl sulphate, two of the three necks of the round-bottomed flask were sealed with rubber septum stoppers, and the flask was transferred to an oil bath on a hotplate stirrer. A reflux condenser was attached to the free neck of the round-bottomed flask, and the hotplate was set to a constant 40° C. using a fuzzy logic temperature control attachment. Once at 40° C., the stirring solution was left under reflux for 4 hours. During this time the solution typically changes colour from colourless to a pale blue. Also note that, whilst not strictly necessary, the degree of sulfonation of the polystyrene tends to increase if the refluxing solution is bubbled gently with argon over the 4 hour period. By increasing the degree of sulfonation, the SPS is found to be more soluble in both acetone and ethyl acetate. The degree of sulfonation is approximately 10%.

After 4 hours, the solution was removed from reflux (and from the argon atmosphere if applicable) and to it was added 50 mL of ethanol. Upon addition, a white precipitate was visible. The solution was gently swirled to aid the distribution of the ethanol throughout the round-bottomed flask before the mixture was poured slowly and carefully into 1.75 L of boiling water. As it was added, the sulfonated polystyrene precipitated rapidly, hence it was necessary to stir the boiling water, preferably through the use of both a magnetic stirrer and a glass/plastic rod operated manually. It was also necessary to add the sulfonated polystyrene solution in stages, removing the precipitate at regular intervals to increase yield. Once complete, the precipitate was washed with water several times before being transferred to a vacuum desiccator for drying. For best results, the precipitate was left overnight to dry. Typically the synthesis, as outlined above, yields ca. 50 g of SPS.

A batch of enhanced polarity sulfonated polystyrene was prepared for use in making indicator compositions that could be used to prepare ethanol based inks. The method used was identical to that described above, except the amount of acetyl sulphonate used in the sulfonation step was increased to 105 mL (i.e., 3 times as much acetyl sulfonate was used). The resulting enhanced polarity sulfonated polystyrene was soluble in ethanol, but insoluble in both ethyl acetate and water. The degree of sulfonation is approximately 30%.

Preparation of Solvent-Based Ink

A solvent based UV activatable, oxygen sensitive ink, in accordance with one embodiment of the present invention, was prepared as follows.

350 mg of SPS was weighed into a small sample vial and to it was added 2 g of acetone. The solution was gently stirred until all the polymer had dissolved. To the solution was then added 250 mg of glycerol (the sacrificial electron donor, SED), and the solution was again gently stirred to improve dissolution thereof.

100 mg of nanorutile titanium dioxide (the photocatalyst) was then added. The solution was then stirred until all of the photocatalyst had dispersed. Once the photocatalyst had fully dispersed, 2.5 mg of methylene blue (the redox active dye) was added, and the resulting solution was sealed in the sample vial using Parafilm (Trade Mark) to mitigate evaporation of acetone. The ink was then stirred, usually overnight, to ensure that all of the methylene blue had dissolved, to provide a solvent based UV activatable, oxygen sensitive ink. Note that 2.5 to 5 mg of methylene blue can be used depending on the desired intensity of "blue" colour. For ethanol based inks, around 30 to 40 mg of methylene blue can be used. This is shown in the ethanol ink example below.

An alternative solvent that can be used in place of acetone is ethyl acetate. It is particularly desirable to use ethyl acetate as most ink manufacturers regard it as a suitable solvent for printing inks. An ethyl acetate based ink was also prepared.

The acetone based ink was found to have a viscosity of 64.7 cP, and the viscosity of the ethyl acetate based ink was found to be 379.6 cP (for reference, water has a viscosity of 0.894 cP and glycerol has a viscosity of 1500 cP). These viscosities make these inks suitable for use in many printing processes such as Gravure printing and flexography.

An alternative solvent that can be used is ethanol, to provide an ethanol based ink. An ethanol based UV activatable, oxygen sensitive ink, in accordance with one embodiment of the present invention, was prepared as follows.

40 mg of methylene blue was added to a sample bottle, to which was added 5 g of ethanol and 2 g of deionised water. The bottle was then closed and sonicated for 10 minutes before the solution was left to gently stir until all the methylene blue had mixed well. After all the methylene blue had dissolved, 500 mg of the enhanced polarity SPS was then added to the solution. The solution formed a gel like substance within the sample bottle as soon as the enhanced polarity SPS was added. The sample bottle was sonicated for approximately 40 minutes, then left to stir gently to facilitate the gel reforming into a solution.

400 mg of glycerol was added to the solution, which was then stirred for 10 to 15 minutes. 300 mg of semi-conductor material (nanorutile titania) was then added to the sample bottle. The sample bottle was then sealed with Parafilm™ to prevent evaporation of the solvent, and the solution was sonicated for a further 5 minutes. The solution was then stirred until all the powder had dispersed.

A further ethanol based ink was prepared as follows. 250 mg of enhanced polarity SPS was weighed into a small sample vial and to it was added 2 g of ethanol. The solution was gently stirred until all the polymer had dissolved. To the solution was then added 250 mg of glycerol (the sacrificial electron donor, SED), and the solution was again gently stirred to improve dissolution thereof.

100 mg of nanorutile titanium dioxide (the photocatalyst) was then added. The solution was then stirred until all of the photocatalyst had dispersed. Once the photocatalyst had fully dispersed, 30 mg of methylene blue (the redox active dye) was added. The resulting solution was sealed in the sample vial, and the ink was stirred to ensure that all of the methylene blue had dissolved, providing a solvent based UV activatable, oxygen sensitive ink.

A further ethanol based ink was prepared using the techniques described above, further incorporating water. The amounts of materials used in the ink were: 3 g of ethanol; 1 g of water; 500 mg of enhanced polarity SPS; 250 mg of trihydroxyhexane; 100 mg of nanorutile titania; and 30 mg of methylene blue.

Film Preparation

Several experiments were carried out in order to test the redox properties of the ink under different conditions. Typically, the ink was cast on to 24 mm glass coverslips using an Electronic Micro Systems Model 4000-1 spin coater. The coverslip was set spinning at 3500 rpm for 30 seconds and 5 drops of the ink were applied, resulting in a blue film. The film can then be used directly without any further treatment (owing to the high spin speed, the film is dry after spin-coating, thus negating the need for a drying step). In the ethyl acetate based examples, the film thickness of the ink is approximately 25 μm, unless otherwise stated.

Barrier layers can be applied on top of an ink film substantially as described above. For example, an ink coated coverslip is spun at a rate of between 500 and 3500 rpm for 30 seconds after the application to the film surface of 1 to 5 drops of the desired barrier layer in liquid form or as a solution.

In order to apply inks to polypropylene, a K-Bar hand application coater, for example, as supplied by RK Print Coat Instruments Ltd, Litlington, Royston, Herts, SG8 0QZ, United Kingdom, is used as follows. A plastic sheet is clamped tightly to a flat surface and a line of ink is deposited at the head of the sheet. The ink is then drawn down the sheet using the desired gauge of K-Bar, before being left to dry. The ink thickness can be varied from 6 μm to 100 μm as necessary using K-Bar 1 to K-Bar 8. Typically, K-Bar 8 is used producing an ink with a thickness of 100 μm when wet. In flexography printing, typically K-Bar 1 or K-Bar 2 is used to coat the ink, which produces a wet layer thickness of 6 μm or 12 μm respectively.

For the testing of polyvinyl alcohol (PVA) barrier layers on polypropylene, the barrier layer is applied using a similar method as described above in relation to the K-Bar, to produce a barrier layer of from 6 μm to 100 μm.

Activation of the Inks

The ink was activated before experimental studies were carried out. To activate the ink, UVA light is required. In brief, irradiation of $TiO_2$ with electromagnetic radiation (i.e. light) of a wavelength less than ca. 380 nm results in the formation of a hole-electron pair. The hole, which is positively charged, reacts with the SED (glycerol) and oxidises it, whilst the negatively charged electron can be used for dye reduction. Reduction of the dye alters its electronic structure, thus causing a colour change to occur.

A 2×8 W, UVA lamp, fitted with Black Light Blue (BLB) bulbs was used to activate the samples. The peak wavelength of UVA light emitted by such bulbs occurs at ca. 365 nm. By placing the lamp flush with the sample under test, a UVA output of ca. 3 mW cm$^{-2}$ is achieved. Ordinarily, around two minutes of UVA irradiation is required to initiate a colour change from blue to colourless for acetone derived compositions. However, by using a higher intensity UVA source, activation of the ink could be achieved more rapidly.

Surprisingly, it has been found that ethyl acetate derived compositions bleach more quickly than acetone derived compositions, typically changing colour after only one minute of exposure to UVA irradiation. Thus ethyl acetate based inks, and the dry compositions therefrom, can be activated twice as quickly as acetone based inks and compositions.

Monitoring of the Film Compositions

The bleaching (UV activation) of the film compositions and their subsequent recovery (oxidation) was recorded photographically. In addition, or alternatively, the recovery of the film compositions was monitored by diffuse reflectance spectroscopy using a hand-held Konica-Minolta CM-2500d Spectrophotometer.

Example 1

An acetone based ink was prepared using the technique described in the general example. A film of the ink was then cast on a coverslip and activated as described above. The so formed film composition was monitored using the diffuse electron spectroscopy technique as described above.

The recovery of the film composition in air at room temperature (approximately 20° C.) was monitored over the course of 16 hours by diffuse reflectance spectroscopy. Under these conditions, a significant degree of blue colour (oxidized methylene blue) appears within 2 to 4 hours.

Example 2

An acetone based ink was prepared using the technique described in the general example. A film of the ink was then cast on a coverslip and activated as described above. The so formed film composition was monitored using the diffuse electron spectroscopy technique as described above.

The recovery of the film composition in air when cooled in a refrigerator (approximately 4° C.) was monitored over the course of 16 hours by diffuse reflectance spectroscopy. Under these conditions, the emergence of the blue colour (oxidized methylene blue) appears more slowly than at room temperature (cf Example 1), taking approximately 16 hours to appear.

Over the course of several days, the blue colour develops for the film compositions of Examples 1 and 2 as the film composition recovers further. Using diffuse reflectance, it is apparent that the ink of Example 1, which is subject to room temperature conditions, recovers more quickly than the ink of Example 2, which is stored in a refrigerator. In any event, it is clear that both inks have developed a significant blue colour after 3 days.

The indicators of Examples 1 and 2 are suitable for use in applications where a relatively quick colour change is required. For example, they may be used in security packaging to indicate when a package has been opened. Such indicators can be included in air-free packages containing, for example, high value items that are often counterfeited. When the package is opened the UV activated indicator is exposed to oxygen and changes colour to reveal text indicating that the item is genuine.

Example 3

An ethyl acetate based ink was prepared using the technique described in the general example. A film of the ink was then cast on a coverslip and activated as described above. The so formed film composition was monitored using the diffuse electron spectroscopy technique as described above.

The recovery of the film composition in air at room temperature (approximately 25° C.) was monitored over the several days by diffuse reflectance spectroscopy. Under these conditions, a significant degree of blue colour (oxidized methylene blue) appears within 2 to 4 hours, and the blue colour has almost completely returned after two days. The rate of recovery was deemed to be similar to, and perhaps slightly faster than, the equivalent acetone based composition.

Example 4

An ethyl acetate based ink was prepared using the technique described in the general example. A film of the ink was then cast on a coverslip and activated as described above. The so formed film composition was monitored using the diffuse electron spectroscopy technique as described above.

The recovery of the film composition in air in a refrigerator (approximately 4° C.) was monitored over the several days by diffuse reflectance spectroscopy. Under these conditions, a no blue colour (oxidized methylene blue) appears within 24 hours. This is in contrast to the equivalent acetone based film composition for which the development of blue colouration was noted after 16 hours.

Further recovery of the composition of Example 4 was monitored and it was noted that under these conditions, no blue colour appeared until between 3 and 6 days. Complete recovery was noted after approximately 10 to 14 days.

Example 5

An acetone based ink was prepared using the technique described in the general example. A film of the ink was then cast on 100 µm polypropylene and activated as described above. The so formed film composition was monitored using the diffuse electron spectroscopy technique as described above.

The recovery of the film composition in air in a refrigerator (approximately 4° C.) was monitored over the several days by diffuse reflectance spectroscopy. Under these conditions, a significant degree of blue colour (oxidized methylene blue) appears within 1 day, and the blue colour has almost completely returned after 14 days.

Example 6

An ethyl acetate based ink was prepared using the technique described in the general example. A film of the ink was then cast on 100 µm polypropylene and activated as described above. The so formed film composition was monitored using the diffuse electron spectroscopy technique as described above.

The recovery of the film composition in air at room temperature (approximately 25° C.) was monitored over the several days by diffuse reflectance spectroscopy. Under these conditions, a significant degree of blue colour (oxidized methylene blue) appears within 1 day, and the blue colour has almost completely returned after 2 to 3 days.

Example 7

An ethyl acetate based ink was prepared using the technique described in the general example. A film of the ink was then cast on 100 µm polypropylene and activated as described above. The so formed film composition was monitored using the diffuse electron spectroscopy technique as described above.

The recovery of the film composition in air in a refrigerator (approximately 4° C.) was monitored over the several days by diffuse reflectance spectroscopy. Under these conditions, a no blue colour (oxidized methylene blue) appears within 3 to 7 days, and the blue colour has almost completely returned after 10 to 14 days.

As mentioned above, each film is irradiated using a 2×8 W UVA source (peak irradiance=365 nm) which is held flush against the sample surface. Naturally this lamp gets very warm, and some of this heat may be transferred to the sample during the irradiation period (2-5 minutes). As demonstrated above, the recovery of the film is clearly affected by temperature; hence there was some concern that the heat from the lamp may potentially influence the recovery profile obtained. Therefore, the following experiment was designed whereby the film was irradiated without being subject to the heat emanating from the lamp.

A quartz cell filled with cold water was placed between the ink film surface and the lamp. This cell effectively acts as a heat barrier, and thus helps prevent the sample from getting too warm. In addition, the amount of UVA irradiation 'lost' is minimised, since both quartz and water are poor UV absorbers at 365 nm. A further sample was prepared and irradiated with UV light without the use of a quartz filter. Both samples were stored in a refrigerator at approximately 4° C.

No significant difference was observed in the recovery profiles obtained for the two inks, both inks appearing to develop a substantial blue colour in 1 day and to have fully recovered within approximately 14 days. Therefore, it would appear that heat transfer from the lamp during irradiation does not have an appreciable effect on the recovery profile obtained.

To increase the length of time of recovery of the ink, further indicators were prepared having barrier layers applied to mitigate exposure to oxygen.

Example 8

An acetone based ink was prepared using the technique described in the general example. A film of the ink was then cast on a coverslip before the application of Sellotape™ having a thickness of 40 µm. On subsequent application of UV light as described above, the ink changed colour from blue to colourless in 2 minutes, suggesting little or no UVA absorbance by the Sellotape™. Thus, it was noted that the Sellotape™ did not affect the rate of bleaching. The Sellotape™ covered film composition was allowed to recover in air at room temperature (approximately 20° C.), and the recovery was monitored using the diffuse electron spectroscopy technique described above.

Example 9

An acetone based ink was prepared using the technique described in the general example. A film of the ink was then cast on a coverslip before the application of Sellotape™ having a thickness of 40 µm. On subsequent application of UV light as described above, the ink changed colour from blue to colourless in 2 minutes, suggesting little or no UVA absorbance by the Sellotape™. Thus, it was noted that the Sellotape™ did not affect the rate of bleaching. The Sellotape™ covered film composition was allowed to recover in air in a refrigerator (approximately 4° C.), and the recovery was monitored using the diffuse electron spectroscopy technique described above.

The recovery over several days of the film composition of Example 8 at room temperature, and the film composition of Example 9 in a refrigerator was monitored by diffuse reflectance. The results indicate that the presence of the barrier layer of Sellotape™ increases the recovery lifetime of the film compositions. In Example 8, any blue colour visible after 3 days is located at the edge of the coverslip, where oxygen is most likely to ingress, and it is only after 7 days that the blue colour becomes visible in the main body of the film. In Example 9, the blue colour which has developed after 7 days is mainly confined to the edge of the film, at the air-film interface, whilst ingress into the bulk of the film appears slower than that observed at room temperature.

Example 10

An ethyl acetate based ink was prepared using the technique described in the general example. A film of the ink was then cast on a coverslip before the application of Sellotape™ having a thickness of 40 µm. The Sellotape™ covered film composition was allowed to recover in air at room temperature (approximately 20° C.), and the recovery was monitored using the diffuse electron spectroscopy technique described above.

Example 11

An ethyl acetate based ink was prepared using the technique described in the general example. A film of the ink was then cast on a coverslip before the application of Sellotape™ having a thickness of 40 µm. The Sellotape™ covered film composition was allowed to recover in air in a refrigerator (approximately 4° C.), and the recovery was monitored using the diffuse electron spectroscopy technique described above.

It was noted from the results that Sellotape™ prolonged the recovery time of the composition. In Example 10, no blue colour was visible until approximately 2 to 3 days, with complete recovery being observed after 9 to 14 days. In Example 11, no blue colour was observed until 6 to 8 days, with complete recovery taking approximately 22 days (as calculated by extrapolation of results measured over 14 days).

Further studies were carried out using Sellotape™, or other types of sticky tape, as barrier layers.

Example 12

An acetone based ink was prepared using the technique described in the general example. A film of the ink was then cast on a coverslip before the application of Sellotape™ having a thickness of 40 µm. On subsequent application of UV light as described above, the film composition changed colour from blue to colourless in 2 minutes, suggesting little or no UVA absorbance by the Sellotape™. Thus, it was noted that the Sellotape™ did not affect the rate of bleaching. The Sellotape™ covered film composition was allowed to recover in air at room temperature (incubated to approximately 25° C.), and the recovery was monitored using the diffuse electron spectroscopy technique described above.

Example 13

An acetone based ink was prepared using the technique described in the general example. A film of the ink was then cast on a coverslip before the application of Sellotape™ having a thickness of 40 µm. On subsequent application of UV light as described above, the film composition changed colour from blue to colourless in 2 minutes, suggesting little or no UVA absorbance by the Sellotape™. Thus, it was noted that the Sellotape™ did not affect the rate of bleaching. The Sellotape™ covered film composition was allowed to recover in air in a refrigerator (approximately 4° C.), and the recovery was monitored using the diffuse electron spectroscopy technique described above.

Again, it is immediately apparent from the diffuse electron spectroscopy measurements that the presence of the barrier layer of Sellotape™ increases the recovery lifetime of the film composition. In Example 12, any blue colour visible after 3 days is located at the edge of the coverslip, where oxygen is most likely to ingress. By 7 days, the film has almost completely recovered its initial blue colour, with full recovery being observed after 8 days.

For Example 13, the results are very different. After 7 days, only a faint blue colour is visible in the film composition. At 7 days, the diffuse reflectance data comparable to that observed after 1 day for Example 12, which is carried out at 25° C. After 14 days, the observed colour resembles that obtained after 2 days at 25° C., which implies that the rate of recovery of the ink is some 7 times slower when the sample is stored in the refrigerator. Extrapolation of recorded diffuse reflectance spectral data for Example 13 estimates that complete recovery of the ink would require approximately 30 days or more.

Sellotape™ is a well recognised brand and is relatively cheap and easy to use. However, there are several variants of Sellotape™. One such variant was purchased and tested for its suitability as a barrier layer. Using a micrometer, its thickness was found to be 33 µm.

Example 14

An acetone based ink was prepared using the technique described in the general example. A film of the ink was then cast on a coverslip before the application of cellulose tape having a thickness of 33 μm. On subsequent application of UV light as described above, the film composition changed colour from blue to colourless in 2 minutes, suggesting little or no UVA absorbance by the cellulose tape. Thus, it was noted that the cellulose tape did not affect the rate of bleaching. The cellulose tape covered film composition was allowed to recover in air at room temperature (incubated to approximately 25° C.), and the recovery was monitored using the diffuse electron spectroscopy technique described above.

Example 15

An acetone based ink was prepared using the technique described in the general example. A film of the ink was then cast on a coverslip before the application of cellulose tape having a thickness of 33 μm. On subsequent application of UV light as described above, the film composition changed colour from blue to colourless in 2 minutes, suggesting little or no UVA absorbance by the cellulose tape. Thus, it was noted that the cellulose tape did not affect the rate of bleaching. The cellulose tape covered film composition was allowed to recover in air in a refrigerator (approximately 4° C.), and the recovery was monitored using the diffuse electron spectroscopy technique described above.

In Example 14 and 15, where there is a layer of 33 μm cellulose tape on the surface of the film composition, again the recovery is much more rapid at 25° C. compared to what is observed at 4° C. Furthermore, the recovery is slightly faster than is observed for 40 μm Sellotape™ under the same conditions. For example, within 5 days, the initial blue colour of the film has fully recovered in the sample stored at 25° C.

After 14 days recovery, the blue colour observed for the Example 15 sample resembles that for the Example 14 sample after 2 days. This again implies that storing the ink at 4° C. slows the recovery by a factor of 7 when compared to storing the sample at 25° C. In Example 15 the original blue colour has still not fully recovered after 2 weeks at 4° C. Extrapolation of the spectral data obtained indicates that complete recovery would require approximately 20 days or more.

Example 16

An ethyl acetate based ink was prepared using the technique described in the general example. A film of the ink was then cast on a coverslip before the application of cellulose tape having a thickness of 33 μm. On subsequent application of UV light as described above, the film composition changed colour from blue to colourless. The cellulose tape covered film composition was allowed to recover in air at room temperature (incubated to approximately 25° C.), and the recovery was monitored using the diffuse electron spectroscopy technique described above.

Example 17

An ethyl acetate based ink was prepared using the technique described in the general example. A film of the ink was then cast on a coverslip before the application of cellulose tape having a thickness of 33 μm. On subsequent application of UV light as described above, the film composition changed colour from blue to colourless. The cellulose tape covered film composition was allowed to recover in air in a refrigerator (at approximately 4° C.), and the recovery was monitored using the diffuse electron spectroscopy technique described above.

The recovery time for the ethyl acetate based film compositions cover with 33 μm cellulose tape, is shorter than for the equivalent film compositions covered with 40 μm Sellotape™. At room temperature, no blue colour was observed for the Sellotape™ covered film until after 2 or 3 days, whereas a blue colour is observable after 1 to 2 days for the 33 μm cellulose tape covered film composition, with complete recovery observed after 7 to 10 days. For the refrigerated examples, blue colour is apparent after 3 to 6 days for the 33 μm cellulose tape examples (c.f. 6 to 8 days for the 40 μm Sellotape™ covered example). Complete recovery in not observed over the 14 day test period, and full recovery is estimated to take ca. 20 days based on extrapolation of data.

Whilst Sellotape™ proved to be an excellent oxygen barrier for the ink, further studies were carried out using alternative barriers in an attempt to vary the amount of time taken for the ink to change colour at both room temperature, and at refrigerator temperature. Thus, further work was undertaken that studied the use of different barrier layers, particularly polymers.

The oxygen barrier properties of a 29 μm adhesive polypropylene layer (supplied by BP Labels Ltd, Cardiff) were studied.

Example 18

An acetone based ink was prepared using the technique described in the general example. A film of the ink was then cast on a coverslip before the application of polypropylene tape having a thickness of 29 μm. On subsequent application of UV light as described above, the film composition changed colour from blue to colourless. The polypropylene tape covered film composition was allowed to recover in air at room temperature (approximately 25° C.), and the recovery was monitored using the diffuse electron spectroscopy technique described above.

Example 19

An acetone based ink was prepared using the technique described in the general example. A film of the ink was then cast on a coverslip before the application of polypropylene tape having a thickness of 29 μm. On subsequent application of UV light as described above, the film composition changed colour from blue to colourless. The polypropylene tape covered film composition was allowed to recover in air in a refrigerator (approximately 4° C.), and the recovery was monitored using the diffuse electron spectroscopy technique described above.

It was noted that the film of Example 18 exhibited a blue colour after 1 day, with complete recovery taking 10 to 14 days. The film of Example 19 exhibited a blue colour after 3 to 7 days with complete recovery taking 18 to 20 days, as estimated by extrapolation of the data measured.

Example 20

An ethyl acetate based ink was prepared using the technique described in the general example. A film of the ink was then cast on a coverslip before the application of polypropylene tape having a thickness of 29 μm. On subsequent application of UV light as described above, the film composition changed colour from blue to colourless. The polypropylene tape covered film composition was allowed to recover in air at room temperature (approximately 25° C.), and the recovery was monitored using the diffuse electron spectroscopy technique described above.

Example 21

An ethyl acetate based ink was prepared using the technique described in the general example. A film of the ink was then cast on a coverslip before the application of polypropylene tape having a thickness of 29 µm. On subsequent application of UV light as described above, the film composition changed colour from blue to colourless. The polypropylene tape covered film composition was allowed to recover in air in a refrigerator (approximately 4° C.), and the recovery was monitored using the diffuse electron spectroscopy technique described above.

It was noted that the film of Example 20 exhibited a blue colour after 2 to 3 days, with complete recovery taking 10 to 14 days. However, the film of Example 21 did not exhibit a significant blue colour until 10 to 14 days.

In addition to adhesive tapes described above, the oxygen barrier properties of three polypropylene sticky-back plastics (SBPs, supplied by Paragon) were also studied. These adhesives are provided with industry names, and hence are herein referred to as follows:

GCTCPP RH01 200 is referred to as SBP200 (thickness=71 µm);
GCTCPP PERM 265 is referred to as SBP265 (thickness=66 µm); and
BCPET36 RP37 220 is referred to as SBP220 (thickness=48 µm).

Similar experiments were conducted to those outlined above. Specifically, the recovery of the film composition with each SBP as a barrier layer was monitored at both 4° C. and 25° C.

Example 22

An acetone based ink was prepared using the technique described in the general example. A film of the ink was then cast on a coverslip before the application of SBP200. On subsequent application of UV light as described above, the film composition changed colour from blue to colourless in 2 minutes, suggesting little or no UVA absorbance by SBP200. Thus, it was noted that SBP200 did not affect the rate of bleaching. SBP200 covered film composition was allowed to recover in air at room temperature (in an incubator at approximately 25° C.), and the recovery was monitored using the diffuse electron spectroscopy technique described above.

Example 23

An acetone based ink was prepared using the technique described in the general example. A film of the ink was then cast on a coverslip before the application of SBP200. On subsequent application of UV light as described above, the film composition changed colour from blue to colourless in 2 minutes, suggesting little or no UVA absorbance by SBP200. Thus, it was noted that SBP200 did not affect the rate of bleaching. SBP200 covered film composition was allowed to recover in air in a refrigerator (approximately 4° C.), and the recovery was monitored using the diffuse electron spectroscopy technique described above.

From the results obtained for the thickest of the three SBPs, SBP200, there is observed a marked difference in the recovery between the two temperatures, the sample at 25° C. (Example 22) having fully recovered within 7 days whilst the sample left recovering at 4° C. (Example 23) appears to recover more slowly in comparison. Indeed, the sample of Example 23 appears to be approximately 5 to 10 times slower to recover in the fridge, with complete recovery observed in 16 to 17 days as estimated by extrapolation of the spectral data.

Example 24

An acetone based ink was prepared using the technique described in the general example. A film of the ink was then cast on a coverslip before the application of SBP265. On subsequent application of UV light as described above, the film composition changed colour from blue to colourless in 2 minutes, suggesting little or no UVA absorbance by SBP265. Thus, it was noted that SBP265 did not affect the rate of bleaching. SBP265 covered film composition was allowed to recover in air at room temperature (in an incubator at approximately 25° C.), and the recovery was monitored using the diffuse electron spectroscopy technique described above.

Example 25

An acetone based ink was prepared using the technique described in the general example. A film of the ink was then cast on a coverslip before the application of SBP265. On subsequent application of UV light as described above, the film composition changed colour from blue to colourless in 2 minutes, suggesting little or no UVA absorbance by SBP265. Thus, it was noted that SBP265 did not affect the rate of bleaching. SBP265 covered film composition was allowed to recover in air in a refrigerator (approximately 4° C.), and the recovery was monitored using the diffuse electron spectroscopy technique described above.

Example 26

An acetone based ink was prepared using the technique described in the general example. A film of the ink was then cast on a coverslip before the application of SBP220. On subsequent application of UV light as described above, the film composition changed colour from blue to colourless in 2 minutes, suggesting little or no UVA absorbance by SBP220. Thus, it was noted that SBP220 did not affect the rate of bleaching. SBP220 covered film composition was allowed to recover in air at room temperature (in an incubator at approximately 25° C.), and the recovery was monitored using the diffuse electron spectroscopy technique described above.

Example 27

An acetone based ink was prepared using the technique described in the general example. A film of the ink was then cast on a coverslip before the application of SBP220. On subsequent application of UV light as described above, the film composition changed colour from blue to colourless in 2 minutes, suggesting little or no UVA absorbance by the SBP220. Thus, it was noted that the SBP220 did not affect the rate of bleaching. The SBP220 covered film composition was allowed to recover in air in a refrigerator (approximately 4° C.), and the recovery was monitored using the diffuse electron spectroscopy technique described above.

In Examples 24, 25, 26 and 27, the samples left to recover at 25° C. had fully recovered their original blue colour within one week, whilst the recovery of the samples at 4° C. was much slower. In Example 25, the sample left to recover in the fridge is estimated to take 20 days to achieve full recovery, whilst the in Example 27, the sample is estimated to fully recover in 16 days under similar conditions. The SBPs would appear to have a similar oxygen barrier quality to that of Sellotape™ and the thinner cellulose tape.

Example 28

An ethyl acetate based ink was prepared using the technique described in the general example. A film of the ink was then cast on a coverslip before the application of SBP200. On subsequent application of UV light as described above, the film composition changed colour from blue to colourless. SBP200 covered film composition was allowed to recover in air at room temperature (in an incubator at approximately 25° C.), and the recovery was monitored using the diffuse electron spectroscopy technique described above.

Example 29

An ethyl acetate based ink was prepared using the technique described in the general example. A film of the ink was then cast on a coverslip before the application of SBP200. On subsequent application of UV light as described above, the film composition changed colour from blue to colourless. SBP200 covered film composition was allowed to recover in air in a refrigerator (approximately 4° C.), and the recovery was monitored using the diffuse electron spectroscopy technique described above.

Example 30

An ethyl acetate based ink was prepared using the technique described in the general example. A film of the ink was then cast on a coverslip before the application of SBP265. On subsequent application of UV light as described above, the film composition changed colour from blue to colourless. SBP265 covered film composition was allowed to recover in air at room temperature (in an incubator at approximately 25° C.), and the recovery was monitored using the diffuse electron spectroscopy technique described above.

Example 31

An ethyl acetate based ink was prepared using the technique described in the general example. A film of the ink was then cast on a coverslip before the application of SBP265. On subsequent application of UV light as described above, the film composition changed colour from blue to colourless. SBP265 covered film composition was allowed to recover in air in a refrigerator (approximately 4° C.), and the recovery was monitored using the diffuse electron spectroscopy technique described above.

Example 32

An ethyl acetate based ink was prepared using the technique described in the general example. A film of the ink was then cast on a coverslip before the application of SBP220. On subsequent application of UV light as described above, the film composition changed colour from blue to colourless. Thus, it was noted that SBP220 did not affect the rate of bleaching. SBP220 covered film composition was allowed to recover in air at room temperature (in an incubator at approximately 25° C.), and the recovery was monitored using the diffuse electron spectroscopy technique described above.

Example 33

An ethyl acetate based ink was prepared using the technique described in the general example. A film of the ink was then cast on a coverslip before the application of SBP220. On subsequent application of UV light as described above, the film composition changed colour from blue to colourless. The SBP220 covered film composition was allowed to recover in air in a refrigerator (approximately 4° C.), and the recovery was monitored using the diffuse electron spectroscopy technique described above.

For the ethyl acetate based film composition allowed to recover at room temperature, a significant blue colour was observed after 1 to 2 days (Examples 28 and 32), or after 2 to 3 days (Example 30). For the compositions that recovered at 4° C., no significant blue colour was observed until 3 to 6 days (Examples 28 and 32), or until in excess of 14 days (Example 30).

Sellotape™, the thinner cellulose tape, polypropylene and the SBPs all proved to be suitable oxygen barriers to lesser or greater degrees. However, it was noted that for the barrier layers tested at 4° C., the blue colour did not emerge until at least approximately 6 to 7 days.

Further materials were studied to assess their suitability as barrier layers. In particular, polymers that can be readily dissolved in a suitable solvent and cast on top of the ink formulation were considered.

One such polymer, which is known to exhibit a strong degree of oxygen impermeability, is polyvinyl alcohol (PVA). A 5% w/w solution of PVA in water can be deposited on top of the ink formulation by spin-coating the PVA solution in a similar way as described above for spin coating the ink formulation onto the coverslips. However, for higher concentrations of PVA (i.e. 10% w/w solution in water), it is necessary to coat the ink onto polypropylene (rather than using a coverslip) and to apply the barrier layer with a K-Bar hand application coater, for example, as supplied by RK Print Coat Instruments Ltd, Litlington, Royston, Herts, SG8 0QZ, United Kingdom.

Example 34

An acetone based ink was prepared using the technique described in the general example. A film of the ink was then cast on a coverslip before the application of 5 drops of a 5% w/w solution of PVA in water by spin-coating at 3500 rpm. On subsequent application of UV light as described above, the film composition changed colour from blue to colourless. The PVA covered film composition was allowed to recover in air at room temperature (approximately 25° C.), and the recovery was monitored using the diffuse electron spectroscopy technique described above.

Example 35

An acetone based ink was prepared using the technique described in the general example. A film of the ink was then cast on a coverslip before the application of 5 drops of a 5% w/w solution of PVA in water by spin-coating at 3500 rpm. On subsequent application of UV light as described above, the film composition changed colour from blue to colourless. The PVA covered film composition was allowed to recover in a refrigerator (approximately 4° C.), and the recovery was monitored using the diffuse electron spectroscopy technique described above.

It was noted that whilst the sample left to recover at 25° C. (Example 34) reacts rapidly, having fully recovered within 3 days, the sample stored at 4° C. (Example 35) is once again much slower to change colour. Indeed, the recovery process appears to be slowed by a factor of approximately 7 for Example 35. For Example, after 7 days the colour of the sample of Example 35 resembles that obtained after 1 day for the sample of Example 34.

Example 36

An ethyl acetate based ink was prepared using the technique described in the general example. A film of the ink was then cast on a coverslip before the application of 5 drops of a 5% w/w solution of PVA in water by spin-coating at 3500 rpm. On subsequent application of UV light as described above, the film composition changed colour from blue to colourless. The PVA covered film composition was allowed to recover in air at room temperature (approximately 25° C.), and the recovery was monitored using the diffuse electron spectroscopy technique described above.

Example 37

An ethyl acetate based ink was prepared using the technique described in the general example. A film of the ink was then cast on a coverslip before the application of 5 drops of a 5% w/w solution of PVA in water by spin-coating at 3500 rpm. On subsequent application of UV light as described above, the film composition changed colour from blue to colourless. The PVA covered film composition was allowed to recover in a refrigerator (approximately 4° C.), and the recovery was monitored using the diffuse electron spectroscopy technique described above.

At room temperature (Example 36) a significant blue colour has appeared after 1 day, and the blue colour returns completely within 2 days. In the refrigerator, however (Example 37), the recovery is much slower with a significant blue colour visible after 2 to 3 days, with recovery increasing (but not complete) up to 15 days from the start of the trial.

Further samples were prepared having PVA thicknesses in the range 6 to 100 μm, on top of the ink film.

Example 38

An acetone based ink was prepared using the technique described in the general example. A film of the ink was then applied to a polypropylene (PP) substrate to a thickness of 100 μm. A 5% w/w solution of PVA in water was applied to the film composition to obtain a PVA coating to a thickness of 100 μm. On subsequent application of UV light as described above, the film composition changed colour from blue to colourless. The PVA covered film composition was allowed to recover in a refrigerator (approximately 4° C.), and the recovery was monitored using the diffuse electron spectroscopy technique described above.

Compared to what is observed when both the ink and PVA barrier layer are spun-coated onto a coverslip, and left to recover in a refrigerator (Example 37), the sample appears to recover more slowly. This is to be expected since spin-coating at 3500 rpm is likely to produce a PVA barrier layer much thinner than 100 μm. It was noted that a significant blue colour was visible after 2 days of recovery.

Example 39

An ethyl acetate based ink was prepared using the technique described in the general example. A film of the ink was then applied to a polypropylene (PP) substrate to a thickness of 100 μm. A 5% w/w solution of PVA in water was applied to the film composition to obtain a PVA coating to a thickness of 100 μm. On subsequent application of UV light as described above, the film composition changed colour from blue to colourless. The PVA covered film composition was allowed to recover at room temperature (approximately 25° C.), and the recovery was monitored using the diffuse electron spectroscopy technique described above.

Example 40

An ethyl acetate based ink was prepared using the technique described in the general example. A film of the ink was then applied to a polypropylene (PP) substrate to a thickness of 100 μm. A 5% w/w solution of PVA in water was applied to the film composition to obtain a PVA coating to a thickness of 100 μm. On subsequent application of UV light as described above, the film composition changed colour from blue to colourless. The PVA covered film composition was allowed to recover in a refrigerator (approximately 4° C.), and the recovery was monitored using the diffuse electron spectroscopy technique described above.

At room temperature, the recovery of the film composition can be seen after 1 day, with complete recovery after 2 to 3 days. In the refrigerator, no significant blue colour appears until 3 to 7 days, with complete recovery observed in 15 days.

Example 41

An acetone based ink was prepared using the technique described in the general example. A film of the ink was then applied to a polypropylene (PP) substrate to a thickness of 100 μm. A 10% w/w solution of PVA in water was applied to the film composition to obtain a PVA coating to a thickness of 60 μm. On subsequent application of UV light as described above, the ink changed colour from blue to colourless. The PVA covered film composition was allowed to recover in a refrigerator (approximately 4° C.), and the recovery was monitored using the diffuse electron spectroscopy technique described above.

Compared to what is observed with a 5% w/w PVA film coated to a thickness of 100 μm (Example 38), the recovery profile obtained when the PVA concentration is increased to 10% w/w and applied to a thickness of 60 μm on top of a 100 μm standard ink film on polypropylene (Example 41) appears to have been slowed further. Indeed, according to the data obtained, no significant blue colour is observed until the fifth day of recovery.

Example 42

An ethyl acetate based ink was prepared using the technique described in the general example. A film of the ink was then applied to a polypropylene (PP) substrate to a thickness of 100 μm. A 10% w/w solution of PVA in water was applied to the film composition to obtain a PVA coating to a thickness of 60 μm. On subsequent application of UV light as described above, the ink changed colour from blue to colourless. The PVA covered film composition was allowed to recover at room temperature (approximately 25° C.), and the recovery was monitored using the diffuse electron spectroscopy technique described above.

Example 43

An ethyl acetate based ink was prepared using the technique described in the general example. A film of the ink was then applied to a polypropylene (PP) substrate to a thickness of 100 μm. A 10% w/w solution of PVA in water was applied to the film composition to obtain a PVA coating to a thickness of 60 µm. On subsequent application of UV light as described above, the ink changed colour from blue to colourless. The PVA covered film composition was allowed to recover in a refrigerator (approximately 4° C.), and the recovery was monitored using the diffuse electron spectroscopy technique described above.

The results obtained for Example 42 and 43 are very similar to those observed for a barrier layer made from a 5% w/w solution of PVA in water. However, the increase in the PVA solution concentration appears to increase the time taken for the films to complete their recovery to the oxidised state. In Example 42 complete recovery is observed after 6 days, and in Example 43 complete recovery is observed after an estimated 16 to 17 days.

Table 1 below provides a summary of all the Examples described above.

TABLE 1

| Formulation (solvent) | Substrate | Barrier | Temp. (° C.) | Time to observe colour | Time for complete recovery |
|---|---|---|---|---|---|
| Example 1 (acetone) | Glass | None | 20 | 2-4 hours | 3 days |
| Example 2 (acetone) | Glass | None | 4 | 16 hours | 14 days |
| Example 3 (ethyl acetate) | Glass | None | 25 | 2-4 hours | 2 days |
| Example 4 (ethyl acetate) | Glass | None | 4 | 2-6 days | 9-14 days |
| Example 5 (acetone) | Polypropylene (100 µm) | None | 4 | 1 day | 14 days |
| Example 6 (ethyl acetate) | Polypropylene (100 µm) | None | 25 | 1 day | 2-3 days |
| Example 7 (ethyl acetate) | Polypropylene (100 µm) | None | 4 | 3-7 days | 10-15 days |
| Example 8 (acetone) | Glass | Sellotape ™ (40 µm) | 20 | 1-2 days | 8 days |
| Example 9 (acetone) | Glass | Sellotape ™ (40 µm) | 4 | 4-7 days | >30 days* |
| Example 10 (ethyl acetate) | Glass | Sellotape ™ (40 µm) | 25 | 2-3 days | 9-14 days |
| Example 11 (ethyl acetate) | Glass | Sellotape ™ (40 µm) | 4 | 6-8 days | 22 days* |
| Example 12 (acetone) | Glass | Sellotape ™ (40 µm) | 25 | 1-2 days | 8 days |
| Example 13 (acetone) | Glass | Sellotape ™ (40 µm) | 4 | 4-7 days | >30 days* |
| Example 14 (acetone) | Glass | Cellulose tape (33 µm) | 25 | 1 day | 5 days |
| Example 15 (acetone) | Glass | Cellulose tape (33 µm) | 4 | 4-7 days | 20 days* |
| Example 16 (ethyl acetate) | Glass | Cellulose tape (33 µm) | 25 | 1-2 days | 7-10 days |
| Example 17 (ethyl acetate) | Glass | Cellulose tape (33 µm) | 4 | 3-6 days | 20 days* |
| Example 18 (acetone) | Glass | Polypropylene (29 µm) | 25 | 1 day | 10-14 days |
| Example 19 (acetone) | Glass | Polypropylene (29 µm) | 4 | 3-7 days | 18-20 days* |
| Example 20 (ethyl acetate) | Glass | Polypropylene (29 µm) | 25 | 2-3 days | 7-10 days |
| Example 21 (ethyl acetate) | Glass | Polypropylene (29 µm) | 4 | 3-6 days | 22 days* |
| Example 22 (acetone) | Glass | SBP 200 (71 µm) | 25 | 1-2 days | 7 days |
| Example 23 (acetone) | Glass | SBP 200 (71 µm) | 4 | 7-10 days | 16-17 days* |
| Example 24 (acetone) | Glass | SBP 265 (66 µm) | 25 | 1-2 days | 7 days |
| Example 25 (acetone) | Glass | SBP 265 (66 µm) | 4 | 7-10 days | 20 days* |
| Example 26 (acetone) | Glass | SBP 220 (48 µm) | 25 | 1-2 days | 7 days |
| Example 27 (acetone) | Glass | SBP 220 (48 µm) | 4 | 3-6 days | 16 days* |
| Example 28 (ethyl acetate) | Glass | SBP 200 (71 µm) | 25 | 1-2 days | 10-14 days |
| Example 29 (ethyl acetate) | Glass | SBP 200 (71 µm) | 4 | 3-6 days | 20 days* |
| Example 30 (ethyl acetate) | Glass | SBP 265 (66 µm) | 25 | 2-3 days | 10-14 days |
| Example 31 (ethyl acetate) | Glass | SBP 265 (66 µm) | 4 | 7-10 days | 22 days* |
| Example 32 (ethyl acetate) | Glass | SBP 220 (48 µm) | 25 | 1-2 days | 10-14 days |

TABLE 1-continued

| Formulation (solvent) | Substrate | Barrier | Temp. (° C.) | Time to observe colour | Time for complete recovery |
|---|---|---|---|---|---|
| Example 33 (ethyl acetate) | Glass | SBP 220 (48 μm) | 4 | 3-6 days | 20 days* |
| Example 34 (acetone) | Glass | 5% w/w PVA | 25 | <1 day | 3 days |
| Example 35 (acetone) | Glass | 5% w/w PVA | 4 | 1-2 days | 14 days |
| Example 36 (ethyl acetate) | Glass | 5% w/w PVA | 25 | 1 day | 2 days |
| Example 37 (ethyl acetate) | Glass | 5% w/w PVA | 4 | 2-3 days | 8-15 days |
| Example 38 (acetone) | Polypropylene (100 μm) | 5% w/w PVA | 4 | 4-7 days | 17 days* |
| Example 39 (ethyl acetate) | Polypropylene (100 μm) | 5% w/w PVA | 25 | 1 day | 2-3 days |
| Example 40 (ethyl acetate) | Polypropylene (100 μm) | 5% w/w PVA | 4 | 3-7 days | 15 days* |
| Example 41 (acetone) | Polypropylene (100 μm) | 10% w/w PVA | 4 | 2-5 days | 14 days |
| Example 42 (ethyl acetate) | Polypropylene (100 μm) | 10% w/w PVA | 25 | 1 day | 6 days |
| Example 43 (ethyl acetate) | Polypropylene (100 μm) | 10% w/w PVA | 4 | 2-6 days | 16-17 days* |

(*denotes estimated recovery times based on spectral data obtained)

Additional studies were carried out wherein an ethyl acetate based ink was applied to the following substrates as supplied by Paragon:
a sheet of material chemically treated with aluminium oxide;
a 12 μm polyester sheet of material; and
a 25 μm oriented polypropylene sheet of material.

It was found in all cases that the ink could be satisfactorily applied to a thickness of 100 μm. Thinner layers can be applied using a K-Bar as described herein. When layers are applied thinly with a K-Bar (for example, 6 μm or 12 μm) it may be necessary, or at least of benefit, to increase the amount of dye in the composition.

Further experiments were carried out to assess the recovery of the indicator inks under "dry" conditions. Dry conditions can be achieved by storing ink films (cast on polypropylene) in small sample vials containing a desiccant, such as silica gel or phosphorous pentoxide.

Example 44

An acetone based ink having a thickness of approximately 100 μm was prepared on a polypropylene sheet using the K-Bar technique described in the general example. A film of the ink was then applied to a polypropylene (PP) substrate. The composition covered PP substrate was placed in a sample vial containing silica gel desiccant. When the sample was placed in the sample vial, the colour was recorded through the glass bottom of the vial, which distorts the diffuse reflectance recording, thereby producing a dark green sample colour.

After 18 hours in the presence of the silica gel, there was no change in the colour of the film. The sample was then irradiated for 10 minutes with UVA radiation, causing the sample to become fully bleached. The sample remained bleached for 21 days in the presence of the silica gel. After 21 days the sample was removed from the sample vial and was allowed to recover in the ambient atmosphere. After 1 day at room temperature in the ambient atmosphere, the sample had recovered a significant blue colour, achieving complete recovery in 6 days.

Example 45

An acetone based ink having a thickness of approximately 100 μm was prepared on a polypropylene sheet using the K-Bar technique described in the general example. A film of the ink was then applied to a polypropylene (PP) substrate. The composition covered PP substrate was placed in a sample vial containing phosphorus pentoxide desiccant. When the sample was placed in the sample vial, the colour was recorded through the glass bottom of the vial, which distorts the diffuse reflectance recording, thereby producing a dark green sample colour.

Similar results were obtained as noted for Example 44.

In view of the above, it is clear that the indicator described herein can also be used to indicate the presence of water.

Example 46

An acetone based ink was prepared using the technique described in the general example. A film of the ink was then cast on a coverslip and activated using UVA as described above. The film composition was monitored using the diffuse electron spectroscopy technique, also as described above.

The recovery of the ink in air in a freezer (approximately −30° C.) was monitored over the course of several days using diffuse reflectance spectroscopy. It is apparent that under these conditions, no blue colour is observed up to 8 days into recovery. Therefore, it is clear that subjecting the indicator composition to reduced temperatures greatly slows the oxidation process.

Example 47

An acetone based ink was prepared using the technique described in the general example. A film of the ink was then cast on a coverslip and activated using UVA as described above. The film composition was monitored using the diffuse electron spectroscopy technique, also as described above.

The recovery of the ink in air in a freezer (approximately −30° C.) was monitored over the course of several days by diffuse reflectance spectroscopy. It is apparent that under these conditions, no blue colour is observed up to 5 days into recovery. The composition was removed from the freezer after 5 days and it is clear that the colour change begins to take place more rapidly, the blue colour emerging after 1 day at room temperature. This blue colour deepens with 2 and 3 days exposure subsequently. Complete recovery of the initial composition colour is estimated to occur in 7 days based on extrapolation of spectral data.

Example 48

An ethyl acetate based ink was prepared using the technique described in the general example. A film of the ink was then cast on a coverslip and activated using UVA as described above. The film composition was monitored using the diffuse electron spectroscopy technique, also as described above.

The recovery of the ink in air in a freezer (approximately −30° C.) was monitored over the course of several days using diffuse reflectance spectroscopy. It is apparent that under these conditions, no blue colour is observed up to 11 days into recovery. Therefore, it is clear that subjecting the indicator composition to reduced temperatures greatly slows the oxidation process.

Therefore, it is clear that subjecting the indicator ink to reduced temperatures greatly slows the recovery (oxidation) process.

Further research indicates that the rate of recovery at room temperature is the same for samples subjected to −30° C. for any length of time (up to and inclusive of one week), as it is for samples which have not been subject to −30° C.

Example 49

An additional study was carried out using an ethanol based ink comprising 250 mg of enhanced polarity SPS and 2 g of ethanol, as described above. A film of the ink was then cast on polypropylene using K-bar 4 (thickness 40 µm). The ink was activated, or bleached, as described above, with only thirty seconds exposure.

The recovery of the ink in air in a refrigerator (approximately 4° C.) was monitored over the course of several days using diffuse reflectance spectroscopy. A blue colour began to appear after approximately 5 days, and complete recovery was noted after approximately 11 days.

In one embodiment the indicator is incorporated into an oxygen indicator for informing a user when a food stuff or the like is no longer fresh, or no longer considered to be fit for consumption. The indicator may be displayed as a dot inside a coloured ring. When the dot changes colour to the extent that it is darker than the ring, the product is no longer fit for consumption.

The indicator can be printed on to the reverse side of an oxygen barrier film. Another film, which is oxygen permeable can be applied such that the ink is sandwiched between the two films. The oxygen permeable film delays the ingress of oxygen to the indicator, and thus increases the amount of time taken for the indicator to change colour. Various reference colours can be placed next to the indicator such that the freshness of the item to which the indicator is applied can be determined. Depending on whether the indicator is placed inside or outside the packaging, this can be used to determine if a package has been inadvertently opened, to determine how long a package has been opened for, or to establish for how long a package has been stored.

The indicator of the present invention can be use as a "best before" type indicator as follows. The indicator is applied to the outside of food or drink packaging by those packaging food (for example, in an in-store bakery or butchers in a supermarket). The ink is activated at the same time as, or just after, application to the packaging. A seal or barrier can be used to delay the colour change of the ink, although this is not always necessary. For example, a suitable varnish or oxygen barrier material can be combined with the ink to delay the colour change.

The ink can therefore be used as a visual indicator to indicate to staff working in a supermarket that goods are nearing, or beyond, the best before date. This will allow staff to quickly identify such goods, thus allowing them to mark them for reduction, or to otherwise dispose of them.

In a further embodiment, barcodes can be printed onto a material onto which has already been applied the indicator ink as described herein. For example, the indicator ink can be applied to the background area of a package onto which a barcode will be printed. The ink is activated so that it is colourless. Over time, the ink oxidises and becomes coloured. As the ink becomes coloured, it obscures the barcode, thus preventing the barcode from being read by barcode scanners. Therefore, in this embodiment, "out of date" goods are highlighted at the point of sale, which enables the prevention of sale of such goods.

In a further embodiment, the indicator is used to indicate when a "consume within a certain time from opening" period has passed. Such periods vary from a few days to several months depending on the nature of the perishable item. The ink can be, for example, applied to the inside of vacuum or controlled atmosphere packaging (thus keeping the ink free from exposure to oxygen). When the packaging is opened, the indicator will be exposed to oxygen and will change colour over a set period of time.

Alternatively, the consume within indicator can be applied to the outside of packaging along with a seal or barrier (if, for example, the oxygen content inside the packaging is too high for the indicator to remain clear). When the packaging is opened, the seal or barrier is also broken allowing the indicator to be exposed to the atmosphere. The indicator will then change colour over a set period of time.

In one embodiment the indicator is incorporated into a water indicator for informing a user when an item has been exposed to moisture. The ink can be applied to the inside of moisture sensitive goods in substantially moisture-free packaging such as dried foods, electrical equipment and pharmaceuticals. If the packaging is compromised, moisture will enter the package and the indicator will change colour thus indicating to the end consumer that the goods that they have received have not been in the required atmospheric conditions and therefore may be spoiled or damaged. In this embodiment, the indicator can also be used to warn manufacturers or distributors that their goods are being exposed to moisture, and that they may need re-packaged, or that they may not be fit for sale.

In one embodiment the indicator ink is incorporated into a time-temperature indicator. Oxidation (but seemingly not reduction) of the indicator composition is temperature sensitive. Once activated, the reduced composition will remain clear if kept at typical domestic freezer temperatures (less than −20° C.). Therefore, the indicator can be used to demonstrate when frozen items have been subject to an increase in temperature. For example, the indicator composition can be applied to a frozen foodstuff and activated using UV light. If the item defrosts, the indicator will change colour, thereby illustrating that the item has been at too high a temperature. If the item is re-frozen, the indicator remains coloured. This can be useful for the consumer, the manufacturer, the distributor and the seller. In particular, the time temperature indicator can be useful for frozen seafood, frozen dairy products (such as ice cream), and frozen poultry, all of which are associated with exponential bacterial growth when exposed to high temperatures (particularly when subsequently re-frozen and defrosted).

In a further embodiment, the indicator ink is incorporated into an anti-counterfeiting device.

The indicator can be applied to the inside of substantially air-free and/or substantially oxygen-free packaging for high value, or often counterfeited goods. When the packaging is opened, a logo or message appears indicating that the goods are genuine. The logo or message can be verified further by applying UV light, which will make the logo or message disappear. The logo or message would then reappear after a short period of time. This could, of course, also be applied to currency and/or documentation.

Examples of Ink in Use

The inks as described above are suitable for use in the printing methods of the present invention, which can be carried out using conventional printing apparatus, for example as used in Gravure printing, flexography printing or screen printing.

In one embodiment, the indicator is provided to a Gravure printer in the form of a printable ink. The Gravure printer is equipped with laminated paper and the printing process is commenced. The printable indicator is applied to the laminated paper in the form of a LOGO or text in the conventional manner using an etched printing cylinder and an impression cylinder as is common in the Gravure process. Once printed, the area of the laminated paper printed with the indicator is sealed by application of polyethylene terephthalate (PET). The section of the laminated paper which is printed with the indicator is then exposed to UV light having a wavelength of about 200-400 nm thereby effecting reduction of a redox sensitive material in the indicator.

In a further embodiment, 2 kg of ink in a glass flask is purged with nitrogen for 15 minutes before irradiation with 12×8 Watt Black Light Blue (BLB) lamps for 24 to 48 hours, whilst stirring. The ink is then provided to a flexographic printer in the form of a printable ink. The flexographic printer is equipped with paper and the printing process is commenced. The printable indicator is applied to the paper in the form of a LOGO or text in the conventional manner as is common in the flexographic process. Once printed, the paper is rolled up on itself, thus preventing the ink from exposure to the atmosphere. The roll of printed paper is then unwound and laminated using conventional laminating techniques. The laminated paper is then used in the manufacture of packing for, for example, foodstuffs.

It will be appreciated that the method can be applied using different types of printing assembly and alternative printing regimes such as web offset printing. Whilst paper and laminated paper are used in the examples given, other suitable printing substrates known in the art can be used. Also, it will be understood that the printable indicator may be applied to the whole, or only a section of, the printing substrate, and that the seal may be applied to the whole, or only a section of, the printing substrate and/or section of the printing substrate to which the indicator is applied. In this embodiment, the printing substrate contains blanks which can be folded to manufacture packages.

The method described can be used to manufacture a blank for a package. In addition, the method described can be used to manufacture a package by folding or arranging a printing substrate or a blank produced using the method.

In the example given, the indicator is sealed using PET. However, it will be appreciated that any suitable seal having a very low oxidising agent permeability (thereby preventing oxidation of the indicator) can be used. Alternatively, the seal may be chosen to provide a semi-permeable seal configured to allow controlled flow of oxidising agent to the indicator. Examples of suitable materials for providing a seal are polyethylene terephthalate (PET), ethylene-vinyl alcohol copolymer (EVOH), polyvinylidene chloride (PVDC), polyvinyl alcohol (PVA) and regenerated cellulose.

The rate of reaction between the reduced form of the redox dye, Red, and oxygen may be rendered mass-transfer dependent, by making the rate of diffusion of oxygen from the ambient air through the film the rate determining step.

The latter can be achieved by making the diffusion process very slow through the use of polymers with low oxygen permeabilities such as polyethylene terephthalate, either as the polymer encapsulating medium or as a film covering the film indicator. Through the use of such a diffusion barrier it is possible to create a type of indicator film that (after photobleaching by UV light) exhibits a recovery time (when exposed to air) that depends upon the thickness of the diffusion barrier film; the thicker the oxygen barrier, the slower the film recovery. When used as an oxygen indicator, in an oxygen-free package, the colour recovery times of this type of indicator can be made sufficiently long (i.e. hours and/or days) that it can provide an indication of how long a modified atmosphere package has been opened, after it is opened and air allowed in.

If a very oxygen impermeable membrane is used as the barrier, the indicator is no longer sensitive towards oxygen and the degree of bleaching the film undergoes upon exposure to UV light can be used as a measure of the level of ambient UV light the film has been exposed to, i.e. such an indicator is a UV-light level indicator.

In the embodiments described, the indictor is in the form of a printable ink and comprises methylene blue (a thiazine dyestuff), glycerol, and nanorutile titanium (IV) oxide ($TiO_2$). The thiazine dyestuff acts as a redox sensitive material, having different visual properties in the oxidised and reduced forms. Other suitable redox sensitive materials include an oxazine dyestuff, an azine dyestuff, a triphenylmethane dyestuff, an indophenol dyestuff, and indigo dyestuff, viologen and/or mixtures thereof. The glycerol acts as an electron donor. Other suitable electron donors include mild reducing agents such as an amine, a reducing saccharide, a readily oxidisable polymer, or other general anti-oxidants.

The $TiO_2$ acts as a semiconductor material specifically sensitive to light having a wavelength of about 200-400 nm. Irradiation of the semiconductor material by light having a wavelength of about 200-400 nm causes an electron to be donated by the electron donor to the semiconductor material which in turn provides an electron to the redox sensitive material causing the redox sensitive material to become reduced. Alternative semiconductor materials include oxides of: titanium, tin, tungsten, zirconium, and zinc and mixtures thereof. In particular the semiconductor material may be selected from one or more the group consisting of: titanium (IV) oxide ($TiO_2$), strontium titanate ($SrTiO_3$), tin (IV) oxide ($SnO_2$), tungsten (IV) oxide ($WO_3$), zirconium (IV) oxide ($ZrO_2$), zinc (II) oxide (ZnO) and mixtures thereof.

Various modifications and variations to the described embodiments of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes of carrying out the invention which are obvious to those skilled in the art are intended to be covered by the present invention.

What is claimed is:

1. An indicator, comprising:
an organic solvent soluble polymer;
a redox sensitive material which displays different visible properties in the oxidized and reduced forms, wherein the redox sensitive material in the oxidized form is bound to the organic solvent soluble polymer by ionic bonding; and
an electron donor; and
wherein the organic solvent soluble polymer is at least partially sulfonated polystyrene which is from about 10% to about 30% sulfonated.

2. The indicator of claim 1, wherein the organic solvent soluble polymer comprises a hydrophobic backbone and a plurality of electronically charged sidechains.

3. The indicator of claim 1, wherein the redox sensitive material comprises one or more of a thiazine dyestuff, an oxazine dyestuff, an azine dyestuff, a triphenylmethane dyestuff, an indophenol dyestuff, an indigo dyestuff, and viologen.

4. The indicator of claim 1, wherein the redox sensitive material comprises methylene blue.

5. The indicator of claim 1, wherein the indicator is supported on an inert material comprising at least one of glass, paper, fabric, plastic, ceramic, and metal.

6. The indicator of claim 5, wherein the inert material has a coating configured to seal at least a portion of the inert material having the indicator applied thereto.

7. The indicator of claim 6, wherein the coating provides a seal that is configured to inhibit oxidation of the indicator.

8. The indicator of claim 6, wherein the coating provides a semi-permeable seal that is configured to allow a controlled flow of an oxidizing agent to the indicator.

9. The indicator of claim 6, wherein the coating is comprised of one or more of PET, EVOH, PVDC, PVA, and regenerated cellulose.

10. The indicator of claim 6, wherein at least a portion of the coating is selectively removable.

11. The indicator of claim 1, wherein the indicator is dissolved in an organic solvent to form an ink.

12. The indicator of claim 11, wherein the organic solvent comprises one or more of acetone, ethyl acetate, and ethanol.

13. The indicator of claim 1, wherein the electron donor comprises at least one of an amine, a reducing saccharide, an oxidizable polymer, a polyol, glycerol, trihydroxyhexane, and a general anti-oxidant.

14. The indicator of claim 1, further comprising at least one semiconductor material that is sensitive to light having a wavelength of about 200-400 nm, and wherein upon irradiation of the semiconductor material by light having a wavelength of about 200-400 nm, an electron is donated by the electron donor to the semiconductor material which in turn provides an electron to the redox sensitive material causing the redox sensitive material to become reduced.

15. The indicator of claim 14, wherein the semiconductor material comprises an oxide of one or more of: titanium, tin, tungsten, zirconium, zinc, and mixtures thereof.

16. A printing substrate comprising the indicator as claimed in claim 1.

17. A blank prepared from the printing substrate as claimed in claim 16.

18. A package prepared from the printing substrate as claimed in claim 16.

19. A method for applying an indicator to a printing substrate, the method comprising:
providing an indicator, the indicator comprising:
an organic solvent soluble polymer; and
a redox sensitive material which displays different visible properties in the oxidized and reduced forms, wherein the redox sensitive material in the oxidized form is bound to the organic solvent soluble polymer by ionic bonding; and
wherein the organic solvent soluble polymer is at least partially sulfonated polystyrene which is from about 10% to about 30% sulfonated;
activating the indicator by reducing the redox sensitive material so as to convert the redox sensitive material into its reduced form;
equipping a printing assembly with the printing substrate;
applying to the printing substrate the activated indicator; and
providing a coating configured to seal at least a portion of the printing substrate having the activated indicator applied thereto.

20. The method of claim 19, wherein the indicator is applied to the printing substrate in the form of a LOGO or text.

21. The method of claim 19, wherein the printing substrate is configured to prepare a blank for use in the manufacture of a package.

22. The method of claim 21, further comprising arranging the blank to form a package.

23. The package prepared from the printing substrate as claimed in claim 22.

24. The blank prepared from the printing substrate as claimed in claim 21.

25. The printing substrate prepared by the method described in claim 19.

* * * * *